US009556229B2

(12) United States Patent
Ruchala et al.

(10) Patent No.: US 9,556,229 B2
(45) Date of Patent: Jan. 31, 2017

(54) MODIFICATION OF PEPTIDES USING A BIS(THIOETHER)ARYLBRIDGE APPROACH

(71) Applicant: The Regents of the University of California, Oakland, CA (US)

(72) Inventors: Piotr Pawel Ruchala, Los Angeles, CA (US); Ewa Dorota Micewicz, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/397,635

(22) PCT Filed: May 17, 2013

(86) PCT No.: PCT/US2013/041650
§ 371 (c)(1),
(2) Date: Oct. 28, 2014

(87) PCT Pub. No.: WO2013/173755
PCT Pub. Date: Nov. 21, 2013

(65) Prior Publication Data
US 2015/0133633 A1 May 14, 2015

Related U.S. Application Data

(60) Provisional application No. 61/649,000, filed on May 18, 2012.

(51) Int. Cl.
*C07K 7/08* (2006.01)
*C07K 1/06* (2006.01)
*C07K 1/107* (2006.01)

(52) U.S. Cl.
CPC ............. *C07K 7/08* (2013.01); *C07K 1/067* (2013.01); *C07K 1/1077* (2013.01)

(58) Field of Classification Search
None
See application file for complete search history.

(56) References Cited

U.S. PATENT DOCUMENTS

| 6,849,714 | B1 | 2/2005 | Bridon et al. | |
|---|---|---|---|---|
| 9,175,056 | B2 | 11/2015 | Nash | |
| 2006/0073518 | A1* | 4/2006 | Timmerman | C40B 30/04 435/7.1 |
| 2007/0207947 | A1 | 9/2007 | Frank et al. | |

FOREIGN PATENT DOCUMENTS

WO   WO 2006/078161   7/2006

OTHER PUBLICATIONS

Chang et al. (2013) "Stapled α-helical peptide drug development: A potent dual inhibitor of MDM2 and MDMX for p53-dependent cancer therapy" *Proc. Natl. Acad. Sci. USA*, 110: E3445-E3454.
Diderich et al. (2016) "Phage Selection of Chemically Stabilized α-Helical Peptide Ligands" *ACS Chem. Biol.* 11(5): 1422-1427; 6 pages.
Kemp and McNamara (1985) "Conformationally Restricted Cyclic Nonapeptides Derived from L-Cysteine and LL-3-Amino-2-piperidone-6-carboxyAlciicd (LL-ACP), a Potent β-Turn-Inducing Dipeptide Analogue" *J. Org. Chem.*, 50: 5834-5838.
Sziewcuk et al. (1992) "Synthesis and biological activity of new conformationally restricted analogues of pepstatin" *Int. J. Peptide Protein Res.*, 40: 233-242.
Timmerman et al. (2005) "Rapid and Quantitative Cyclization of Multiple Peptide Loops onto Synthetic Scaffolds for Structural Mimicry of Protein Surfaces" *ChemBioChem* 6(5):821-824.
PCT International Search Report and Written Opinion dated Aug. 23, 2013 issued in PCT/US2013/041650.
PCT International Preliminary Report on Patentability and Written Opinion dated Nov. 18, 2014 issued in PCT/US2013/041650.
Cardoso et al. (2007) "Structural Basis of Enhanced Binding of Extended and Helically Constrained Peptide Epitopes of the Broadly Neutralizing HIV-1 Antibody 4E10" *Journal of Molecular Biology* 365(5):1533-1544.
Doss et al. (2012) "Hapivirins and Diprovirins: Novel θ-Defensin Analogs with Potent Activity against Influenza A Virus" *J. Immunol.*, 188(6):2759-2768.
Fulda et al. (2012) "Targeting IAP proteins for therapeutic intervention in cancer" *Nat. Rev. Drug. Discov.* 11(2): 109-123.
Isaad et al. (2009) "Side chain-to-side chain cyclization by click reaction" *J. Pept. Sci.*, 15(7): 451-454.
Li et al. (2010) "Systematic mutational analysis of peptide inhibition of the p53-MDM2/MDMX interactions." *J. Mol. Biol.* 398:200 [NIH Public Access—Author Manuscript].
Liu et al. (2010) "D-peptide inhibitors of the p53—MDM2 interaction for targeted molecular therapy of malignant neoplasms" *Proc. Natl. Acad. Sci. USA*, 107(32): 14321-14326.
Locatelli et al. (2009) "Hematide™ for the treatment of chronic kidney disease-related anemia" *Expert. Rev. Hematol.*, 2(4): 377-383 [(www.interscience.com) DOI 10.1002/psc.1141].
Macdougall et al. (2009) "A Peptide-Based Erythropoietin-Receptor Agonist for Pure Red-Cell Aplasia" *N. Engl. J. Med.* 361(19): 1848-1855.
Moller (2011) "Synthesis, characterisation, and mass spectrometric detection of a pegylated EPO-mimetic peptide for sports drug testing purposes" *Rapid Commun. Mass Spectrom.* 25(15): 2115-2123.
Pazgiera et al. (2009) "Structural basis for high-affinity peptide inhibition of p53 interactions with MDM2 and MDMX" *Proc. Natl. Acad. Sci. USA*, 106(12): 4665-4670.
Peng et al. (2012) "Bivalent Smac Mimetics with a Diazabicyclic Core as Highly Potent Antagonists of XIAP and cIAP1/2 and Novel Anticancer Agents" *J. Med. Chem.*, 55(1): 106-114.
Ruchala et al. (2011) "Simplified theta-defensins: search for new antivirals." *Int. J. Pept. Res. Ther.* 17(4): 325-336.

(Continued)

*Primary Examiner* — Thomas S Heard
(74) *Attorney, Agent, or Firm* — Tom Hunter; Weaver Austin Villeneuve & Sampson LLP

(57) ABSTRACT

This invention provides novel methods of stabilizing peptides and peptides so stabilized. In certain embodiments the methods involve providing a peptide containing at least two S bearing residues within the peptide; and reacting the peptide with a di-halogen-aryl-compounds to form a bis (thioether)-aryl-bridge between said two residues.

15 Claims, 13 Drawing Sheets

(56) References Cited

OTHER PUBLICATIONS

Salvatore et al. (2005) "A mild and highly convenient chemoselective alkylation of thiols using $Cs_2CO_3$-TBAI" *Tetrahedron Lett* 46: 8931-8935.

Smith (2010) "Apolipoprotein A-I and its mimetics for the treatment of atherosclerosis" *Curr. Opin. Investig. Drugs*, 11(9): 989-996.

Su et al. (2010) "Apolipoprotein A-I (apoA-I) and apoA-I mimetic peptides inhibit tumor development in a mouse model of ovarian cancer." *Proc. Natl. Acad. Sci. USA*, 107(46): 19997-20002.

Sun et al. (2011) "Potent Bivalent Smac Mimetics: Effect of the Linker on Binding to Inhibitor of Apoptosis Proteins (IAPs) and Anticancer Activity" *J. Med. Chem.* 54 (9): 3306-3318 [NIH Public Access—Author Manuscript].

Van Lenten et al. (2009) "Apolipoprotein A-I Mimetic Peptides" *Curr. Atheroscler. Rep.* 11(1): 52-57 [NIH Public Access—Author Manuscript].

Woodburn et al. (2010) "A subchronic murine intravenous pharmacokinetic and toxicity study of Hematide™, a PEGylated peptidic erythropoiesis-stimulating agent." *Drug Chem. Toxicol.*, 33(1): 28-37.

* cited by examiner

DpV13

DpV13ST

DpV13STOX

*Fig. 6A, cont'd.*

SEQUENCE LISTING

<160> NUMBER OF SEQ ID NOS: 69

<210> SEQ ID NO 1
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Epsilon-aminocaproic acid

<400> SEQUENCE: 1

Asp Xaa Phe Lys Cys Phe Tyr Cys Lys Val Ala Glu Cys Phe Lys Cys
1               5                   10                  15

Ala Phe

<210> SEQ ID NO 2
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (6)..(6)
<223> OTHER INFORMATION: D tyrosine
<220> FEATURE:
<221> NAME/KEY: misc_feature
<222> LOCATION: (10)..(10)
<223> OTHER INFORMATION: D leucine

<400> SEQUENCE: 2

Thr Ser Phe Ala Glu Xaa Trp Ala Leu Xaa Ser Pro
1               5                   10

<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Ser Gln Glu Thr Phe Ser Asp Leu Trp Lys Leu Leu Pro Glu Asn
1               5                   10                  15

<210> SEQ ID NO 4
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (9)..(9)
<223> OTHER INFORMATION: D alanine

<400> SEQUENCE: 4

Thr Ser Phe Ala Cys Tyr Trp Cys Ala Leu Ser Pro
1               5                   10

<210> SEQ ID NO 5
<211> LENGTH: 11

```
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Pentafluoro-(L)-phenylalanine
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (7)..(7)
<223> OTHER INFORMATION: Cyclohexyl-(L)-alanine
<220> FEATURE:
<221> NAME/KEY: misc_feature
<222> LOCATION: (9)..(9)
<223> OTHER INFORMATION: D alanine
<220> FEATURE:
<221> NAME/KEY: misc_feature
<222> LOCATION: (10)..(10)
<223> OTHER INFORMATION: Cyclohexyl-(L)-alanine

<400> SEQUENCE: 5

Thr Ser Xaa Ala Xaa Tyr Xaa Cys Ala Xaa Ser
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D arginine
<220> FEATURE:
<221> NAME/KEY: misc_feature
<222> LOCATION: (3)..(3)
<223> OTHER INFORMATION: 2-Naphthyl-(L)-alanine
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (7)..(7)
<223> OTHER INFORMATION: 1-Naphthyl-(L)-alanine
<220> FEATURE:
<221> NAME/KEY: misc_feature
<222> LOCATION: (9)..(9)
<223> OTHER INFORMATION: D arginine
<220> FEATURE:
<221> NAME/KEY: misc_feature
<222> LOCATION: (10)..(10)
<223> OTHER INFORMATION: Cyclohexyl-(L)-alanine

<400> SEQUENCE: 6

Xaa Arg Xaa Arg Xaa Tyr Xaa Cys Xaa Xaa Arg
1               5                   10

<210> SEQ ID NO 7
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D arginine
<220> FEATURE:
```

-continued

```
<221> NAME/KEY: misc_feature
<222> LOCATION: (3)..(3)
<223> OTHER INFORMATION: Pentafluoro-(L)-phenylalanine
<220> FEATURE:
<221> NAME/KEY: misc_feature
<222> LOCATION: (5)..(5)
<223> OTHER INFORMATION: C cysteine
<220> FEATURE:
<221> NAME/KEY: misc_feature
<222> LOCATION: (7)..(7)
<223> OTHER INFORMATION: aphthyl-(L)-alanine
<220> FEATURE:
<221> NAME/KEY: misc_feature
<222> LOCATION: (9)..(9)
<223> OTHER INFORMATION: D arginine
<220> FEATURE:
<221> NAME/KEY: misc_feature
<222> LOCATION: (10)..(10)
<223> OTHER INFORMATION: Cyclohexyl-(L)-alanine

<400> SEQUENCE: 7

Xaa Arg Xaa Arg Xaa Tyr Xaa Cys Xaa Xaa Arg
1               5                   10

<210> SEQ ID NO 8
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D arginine
<220> FEATURE:
<221> NAME/KEY: misc_feature
<222> LOCATION: (3)..(1)
<223> OTHER INFORMATION: Pentafluoro-(L)-phenylalanine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (7)..(7)
<223> OTHER INFORMATION: 1-Naphthyl-(L)-alanine
<220> FEATURE:
<221> NAME/KEY: misc_feature
<222> LOCATION: (9)..(9)
<223> OTHER INFORMATION: D arginine
<220> FEATURE:
<221> NAME/KEY: misc_feature
<222> LOCATION: (10)..(10)
<223> OTHER INFORMATION: Cyclohexyl-(L)-alanine

<400> SEQUENCE: 8

Xaa Arg Xaa Arg Xaa Tyr Xaa Cys Xaa Xaa Arg
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Epsilon-aminocaproic acid
<220> FEATURE:
<221> NAME/KEY: misc_feature
```

```
<222> LOCATION: (2)..(2)
<223> OTHER INFORMATION: D arginine
<220> FEATURE:
<221> NAME/KEY: misc_feature
<222> LOCATION: (4)..(4)
<223> OTHER INFORMATION: Pentafluoro-(L)-phenylalanine
<220> FEATURE:
<221> NAME/KEY: misc_feature
<222> LOCATION: (6)..(6)
<223> OTHER INFORMATION: D cysteine
<220> FEATURE:
<221> NAME/KEY: misc_feature
<222> LOCATION: (8)..(8)
<223> OTHER INFORMATION: 1-Naphthyl-(L)-alanine
<220> FEATURE:
<221> NAME/KEY: misc_feature
<222> LOCATION: (10)..(10)
<223> OTHER INFORMATION: D arginine
<220> FEATURE:
<221> NAME/KEY: misc_feature
<222> LOCATION: (11)..(11)
<223> OTHER INFORMATION: Cyclohexyl-(L)-alanine

<400> SEQUENCE: 9

Xaa Xaa Arg Xaa Arg Xaa Tyr Xaa Cys Xaa Xaa Arg
1               5                   10

<210> SEQ ID NO 10
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Epsilon-aminocaproic acid
<220> FEATURE:
<221> NAME/KEY: misc_feature
<222> LOCATION: (3)..(3)
<223> OTHER INFORMATION: Epsilon-aminocaproic acid
<220> FEATURE:
<221> NAME/KEY: misc_feature
<222> LOCATION: (4)..(4)
<223> OTHER INFORMATION: D arginine
<220> FEATURE:
<221> NAME/KEY: misc_feature
<222> LOCATION: (6)..(6)
<223> OTHER INFORMATION: Pentafluoro-(L)-phenylalanine
<220> FEATURE:
<221> NAME/KEY: misc_feature
<222> LOCATION: (8)..(8)
<223> OTHER INFORMATION: D cysteine
<220> FEATURE:
<221> NAME/KEY: misc_feature
<222> LOCATION: (10)..(10)
<223> OTHER INFORMATION: 1-Naphthyl-(L)-alanine
<220> FEATURE:
<221> NAME/KEY: misc_feature
<222> LOCATION: (12)..(2)
<223> OTHER INFORMATION: D arginine
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Cyclohexyl-(L)-alanine

<400> SEQUENCE: 10

Xaa Lys Xaa Xaa Arg Xaa Arg Xaa Tyr Xaa Cys Xaa Xaa Arg
1               5                   10

<210> SEQ ID NO 11
```

```
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Epsilon-aminocaproic acid
<220> FEATURE:
<221> NAME/KEY: misc_feature
<222> LOCATION: (3)..(3)
<223> OTHER INFORMATION: Epsilon-aminocaproic acid
<220> FEATURE:
<221> NAME/KEY: misc_feature
<222> LOCATION: (4)..(4)
<223> OTHER INFORMATION: D arginine
<220> FEATURE:
<221> NAME/KEY: misc_feature
<222> LOCATION: (6)..(6)
<223> OTHER INFORMATION: Pentafluoro-(L)-phenylalanine
<220> FEATURE:
<221> NAME/KEY: misc_feature
<222> LOCATION: (8)..(8)
<223> OTHER INFORMATION: D cysteine
<220> FEATURE:
<221> NAME/KEY: misc_feature
<222> LOCATION: (10)..(10)
<223> OTHER INFORMATION: 1-Naphthyl-(L)-alanine
<220> FEATURE:
<221> NAME/KEY: misc_feature
<222> LOCATION: (12)..(12)
<223> OTHER INFORMATION: D arginine
<220> FEATURE:
<221> NAME/KEY: misc_feature
<222> LOCATION: (13)..(13)
<223> OTHER INFORMATION: Cyclohexyl-(L)-alanine

<400> SEQUENCE: 11

Xaa Tyr Xaa Xaa Arg Xaa Arg Xaa Lys Xaa Cys Xaa Xaa Arg
1               5                   10

<210> SEQ ID NO 12
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Epsilon-aminocaproic acid
<220> FEATURE:
<221> NAME/KEY: misc_feature
<222> LOCATION: (2)..(2)
<223> OTHER INFORMATION: D arginine
<220> FEATURE:
<221> NAME/KEY: misc_feature
<222> LOCATION: (4)..(4)
<223> OTHER INFORMATION: Pentafluoro-(L)-phenylalanine
<220> FEATURE:
<221> NAME/KEY: misc_feature
<222> LOCATION: (6)..(6)
<223> OTHER INFORMATION: D cysteine
<220> FEATURE:
<221> NAME/KEY: misc_feature
<222> LOCATION: (8)..(8)
<223> OTHER INFORMATION: 1-Naphthyl-(L)-alanine
<220> FEATURE:
<221> NAME/KEY: misc_feature
<222> LOCATION: (10)..(10)
<223> OTHER INFORMATION: D arginine
<220> FEATURE:
<221> NAME/KEY: misc_feature
<222> LOCATION: (11)..(11)
<223> OTHER INFORMATION: Cyclohexyl-(L)-alanine
```

<400> SEQUENCE: 12

Xaa Xaa Arg Xaa Arg Xaa Tyr Xaa Cys Xaa Xaa Arg
1               5                   10

<210> SEQ ID NO 13
<211> LENGTH: 11
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: D arginine
<220> FEATURE:
<221> NAME/KEY: misc_feature
<222> LOCATION: (3)..(3)
<223> OTHER INFORMATION: Pentafluoro-(L)-phenylalanine
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (7)..(7)
<223> OTHER INFORMATION: 1-Naphthyl-(L)-alanine
<220> FEATURE:
<221> NAME/KEY: misc_feature
<222> LOCATION: (9)..(9)
<223> OTHER INFORMATION: D arginine
<220> FEATURE:
<221> NAME/KEY: misc_feature
<222> LOCATION: (10)..(10)
<223> OTHER INFORMATION: Cyclohexyl-(L)-alanine

<400> SEQUENCE: 13

Xaa Arg Xaa Arg Xaa Tyr Xaa Cys Xaa Xaa Arg
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic peptide

<400> SEQUENCE: 14

Thr Ser Phe Arg Arg Tyr Cys Arg Arg Cys Ser Pro
1               5                   10

<210> SEQ ID NO 15
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (10)..(10)
<223> OTHER INFORMATION: D cysteine

<400> SEQUENCE: 15

Thr Ser Phe Arg Arg Tyr Cys Arg Arg Xaa Ser Pro
1               5                   10

<210> SEQ ID NO 16
<211> LENGTH: 12
<212> TYPE: PRT
<213> ORGANISM: Artificial
<220> FEATURE:
<223> OTHER INFORMATION: Synthetic peptide

<400> SEQUENCE: 16

Thr Ser Phe Arg Arg Tyr Cys Arg Arg Cys Ser Pro
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (10)..(10)
<223> OTHER INFORMATION: D cysteine

<400> SEQUENCE: 17

Thr Ser Phe Arg Arg Tyr Cys Arg Arg Xaa Ser Pro
1               5                   10

<210> SEQ ID NO 18
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (9)..(9)
<223> OTHER INFORMATION: D cysteine

<400> SEQUENCE: 18

Thr Ser Phe Ala Xaa Tyr Trp Gly Xaa Leu Ser Pro
1               5                   10

<210> SEQ ID NO 19
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: D cysteine

<400> SEQUENCE: 19

Thr Ser Phe Ala Cys Tyr Trp Gly Xaa Leu Ser Pro
1               5                   10

<210> SEQ ID NO 20
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (9)..(9)
<223> OTHER INFORMATION: D cysteine

<400> SEQUENCE: 20

Thr Ser Phe Ala Xaa Tyr Trp Gly Xaa Leu Ser Pro
1               5                   10

<210> SEQ ID NO 21
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: D cysteine

<400> SEQUENCE: 21

Thr Ser Phe Ala Cys Tyr Trp Gly Xaa Leu Ser Pro
1               5                   10

<210> SEQ ID NO 22
<211> LENGTH: 11
<212> TYPE: PRT
<213> ORGANISM: Artificial
<220> FEATURE:
<223> OTHER INFORMATION: Synthetic peptide

<400> SEQUENCE: 22

Arg Phe Cys Arg Tyr Trp Cys Arg Leu Arg Pro
1               5                   10

<210> SEQ ID NO 23
<211> LENGTH: 11
<212> TYPE: PRT
<213> ORGANISM: Artificial
<220> FEATURE:
<223> OTHER INFORMATION: Synthetic peptide

<400> SEQUENCE: 23

Arg Phe Cys Arg Tyr Trp Cys Arg Leu Arg Pro
1               5                   10

<210> SEQ ID NO 24
<211> LENGTH: 11
<212> TYPE: PRT
<213> ORGANISM: Artificial
<220> FEATURE:
<223> OTHER INFORMATION: Synthetic peptide

<400> SEQUENCE: 24

Arg Phe Cys Arg Tyr Trp Cys Arg Leu Arg Pro
1               5                   10

<210> SEQ ID NO 25
<211> LENGTH: 11
<212> TYPE: PRT
<213> ORGANISM: Artificial
<220> FEATURE:
<223> OTHER INFORMATION: Synthetic peptide

<400> SEQUENCE: 25

Arg Phe Cys Arg Tyr Trp Cys Arg Leu Arg Pro
1               5                   10

<210> SEQ ID NO 26
<211> LENGTH: 11
<212> TYPE: PRT
<213> ORGANISM: Artificial
<220> FEATURE:
<223> OTHER INFORMATION: Synthetic peptide

<400> SEQUENCE: 26

Arg Phe Cys Arg Tyr Trp Cys Arg Leu Arg Pro
1               5                   10

<210> SEQ ID NO 27
<211> LENGTH: 11
<212> TYPE: PRT
<213> ORGANISM: Artificial
<220> FEATURE:
<223> OTHER INFORMATION: Synthetic peptide

<400> SEQUENCE: 27

Arg Phe Cys Arg Tyr Trp Cys Arg Leu Arg Pro
1               5                   10

<210> SEQ ID NO 28
<211> LENGTH: 22
<212> TYPE: PRT
<213> ORGANISM: Artificial
<220> FEATURE:
<223> OTHER INFORMATION: Synthetic peptide

<400> SEQUENCE: 28

Arg Phe Cys Arg Tyr Trp Cys Arg Leu Arg Pro Arg Phe Cys Arg Tyr
1               5                   10                  15

Trp Cys Arg Leu Arg Pro
            20

<210> SEQ ID NO 29
<211> LENGTH: 22
<212> TYPE: PRT
<213> ORGANISM: Artificial
<220> FEATURE:
<223> OTHER INFORMATION: Synthetic peptide

<400> SEQUENCE: 29

Arg Phe Cys Arg Tyr Trp Cys Arg Leu Arg Pro Arg Phe Cys Arg Tyr
1               5                   10                  15

Trp Cys Arg Leu Arg Pro
            20

<210> SEQ ID NO 30
<211> LENGTH: 11
<212> TYPE: PRT
<213> ORGANISM: Artificial
<220> FEATURE:
<223> OTHER INFORMATION: Synthetic peptide

<400> SEQUENCE: 30

Arg Phe Cys Arg Tyr Trp Cys Arg Leu Arg Pro
1               5                   10

<210> SEQ ID NO 31
<211> LENGTH: 11
<212> TYPE: PRT
<213> ORGANISM: Artificial
<220> FEATURE:
<223> OTHER INFORMATION: Synthetic peptide

<400> SEQUENCE: 31

Arg Phe Cys Arg Tyr Trp Cys Arg Leu Arg Pro
1               5                   10

<210> SEQ ID NO 32

<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: D cysteine

<400> SEQUENCE: 32

Thr Ser Phe Ala Cys Tyr Trp Gly Xaa Leu Ser Pro
1               5                   10

<210> SEQ ID NO 33
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: D alanine

<400> SEQUENCE: 33

Thr Cys Phe Ala Gly Tyr Trp Cys Xaa Leu Ser Pro
1               5                   10

<210> SEQ ID NO 34
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: D alanine

<400> SEQUENCE: 34

Thr Cys Phe Ala Gly Tyr Trp Cys Xaa Leu Ser Pro
1               5                   10

<210> SEQ ID NO 35
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: D cysteine

<400> SEQUENCE: 35

Thr Cys Phe Ala Gly Tyr Trp Gly Xaa Leu Ser Pro
1               5                   10

<210> SEQ ID NO 36
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: D cysteine

<400> SEQUENCE: 36

```
Thr Cys Phe Ala Gly Tyr Trp Gly Xaa Leu Ser Pro
1               5                   10

<210> SEQ ID NO 37
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Beta-homo-(L)-proline
<220> FEATURE:
<221> NAME/KEY: misc_feature
<222> LOCATION: (4)..(4)
<223> OTHER INFORMATION: D tryptophan
<220> FEATURE:
<221> NAME/KEY: misc_feature
<222> LOCATION: (6)..(6)
<223> OTHER INFORMATION: D lysine
<220> FEATURE:
<221> NAME/KEY: misc_feature
<222> LOCATION: (7)..(7)
<223> OTHER INFORMATION: Isonipecotic acid

<400> SEQUENCE: 37

Xaa Arg Ala Xaa Arg Xaa Xaa
1               5

<210> SEQ ID NO 38
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is any amino acid

<400> SEQUENCE: 38

Xaa Xaa Pro Xaa
1

<210> SEQ ID NO 39
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is L-phenylglycine

<400> SEQUENCE: 39
```

Xaa Xaa Pro Xaa
1

<210> SEQ ID NO 40
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (3)..(3)
<223> OTHER INFORMATION: Xaa is N-Methyl-(L)-phenylglycine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 40

Xaa Xaa Pro Xaa
1

<210> SEQ ID NO 41
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is 4-(Aminomethyl)phenylpropionic acid

<400> SEQUENCE: 41

Xaa Xaa Pro Xaa
1

<210> SEQ ID NO 42
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is (R,S)-1,3-Dihydro-2H-isoindole
      carboxylic acid

```
<400> SEQUENCE: 42

Xaa Xaa Pro Xaa
1

<210> SEQ ID NO 43
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is (S)-Indoline-2-carboxylic acid

<400> SEQUENCE: 43

Xaa Xaa Pro Xaa
1

<210> SEQ ID NO 44
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is cyclohexylglycine

<400> SEQUENCE: 44

Xaa Xaa Pro Xaa
1

<210> SEQ ID NO 45
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is trans-4-(aminomethyl)cyclohexanoic acid

<400> SEQUENCE: 45

Xaa Xaa Pro Xaa
1
```

```
<210> SEQ ID NO 46
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine

<400> SEQUENCE: 46

Xaa Xaa Pro Phe
1

<210> SEQ ID NO 47
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is Pentafluoro-(L)-phenylalanine

<400> SEQUENCE: 47

Xaa Xaa Pro Xaa
1

<210> SEQ ID NO 48
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is beta-homo-(L)-phenylalanine

<400> SEQUENCE: 48

Xaa Xaa Pro Xaa
1

<210> SEQ ID NO 49
<211> LENGTH: 4
<212> TYPE: PRT
<213> ORGANISM: Artificial
<220> FEATURE:
<223> OTHER INFORMATION: Synthetic peptide
```

```
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is (3S)-1,2,3,4-tetrahydroisoquinoline-3-
      carboxylic acid

<400> SEQUENCE: 49

Xaa Xaa Pro Xaa
1

<210> SEQ ID NO 50
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is Cyclohexyl-(L)-alanine

<400> SEQUENCE: 50

Xaa Xaa Pro Xaa
1

<210> SEQ ID NO 51
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is beta-homo-(S,R)-naphthylglycine

<400> SEQUENCE: 51

Xaa Xaa Pro Xaa
1

<210> SEQ ID NO 52
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
```

<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is 1-Naphthyl-(L)-alanine

<400> SEQUENCE: 52

Xaa Xaa Pro Xaa
1

<210> SEQ ID NO 53
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is 1-Naphthyl-(L)-alanine

<400> SEQUENCE: 53

Xaa Xaa Pro Xaa
1

<210> SEQ ID NO 54
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is 1-Naphthyl-(L)-alanine

<400> SEQUENCE: 54

Xaa Xaa Pro Xaa
1

<210> SEQ ID NO 55
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)

```
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is 2-naphthyl-(L)-alanine

<400> SEQUENCE: 55

Xaa Xaa Pro Xaa
1

<210> SEQ ID NO 56
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is 3,3-diphenyl-(L)-alanine

<400> SEQUENCE: 56

Xaa Xaa Pro Xaa
1

<210> SEQ ID NO 57
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is biphenylalanine

<400> SEQUENCE: 57

Xaa Xaa Pro Xaa
1

<210> SEQ ID NO 58
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
```

-continued

```
<223> OTHER INFORMATION: Xaa is biphenylalanine

<400> SEQUENCE: 58

Xaa Xaa Pro Xaa
1

<210> SEQ ID NO 59
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is biphenylalanine

<400> SEQUENCE: 59

Xaa Xaa Pro Xaa
1

<210> SEQ ID NO 60
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 60

Xaa Xaa Pro Xaa
1

<210> SEQ ID NO 61
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is N-methyl-L-alanine
<220> FEATURE:
<221> NAME/KEY: misc_feature
<222> LOCATION: (2)..(2)
<223> OTHER INFORMATION: Xaa is L-tert-leucine

<400> SEQUENCE: 61

Xaa Xaa Pro Trp
1
```

```
<210> SEQ ID NO 62
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Naphthyl-(L)-alanine
<220> FEATURE:
<221> NAME/KEY: misc_feature
<222> LOCATION: (5)..(2)
<223> OTHER INFORMATION: D cysteine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: D cysteine

<400> SEQUENCE: 62

Asp Xaa Phe Lys Xaa Phe Tyr Cys Lys Val Ala Glu Xaa Phe Lys Cys
1               5                   10                  15

Ala Phe

<210> SEQ ID NO 63
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Naphthyl-(L)-alanine
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (13)..(13)
<223> OTHER INFORMATION: D cysteine

<400> SEQUENCE: 63

Asp Xaa Phe Lys Xaa Phe Tyr Cys Lys Val Ala Glu Xaa Phe Lys Cys
1               5                   10                  15

Ala Phe

<210> SEQ ID NO 64
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Naphthyl-(L)-alanine
<220> FEATURE:
<221> NAME/KEY: misc_feature
<222> LOCATION: (5)..(5)
<223> OTHER INFORMATION: D cysteine
<220> FEATURE:
<221> NAME/KEY: misc_feature
<222> LOCATION: (13)..(13)
<223> OTHER INFORMATION: D cysteine

<400> SEQUENCE: 64
```

```
Asp Xaa Phe Lys Xaa Phe Tyr Cys Lys Val Ala Glu Xaa Phe Lys Cys
1               5                   10                  15
Ala Phe
```

<210> SEQ ID NO 65
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: D proline

<400> SEQUENCE: 65

```
Ile Cys Arg Ile Ile Ile Xaa Pro Ile Arg Ile Ile Cys
1               5                   10
```

<210> SEQ ID NO 66
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: D proline

<400> SEQUENCE: 66

```
Ile Cys Arg Ile Ile Ile Xaa Pro Ile Arg Ile Ile Cys
1               5                   10
```

<210> SEQ ID NO 67
<211> LENGTH: 13
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: D proline

<400> SEQUENCE: 67

```
Ile Cys Arg Ile Ile Ile Xaa Pro Ile Arg Ile Ile Cys
1               5                   10
```

<210> SEQ ID NO 68
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Epsilon-aminocaproic acid

<400> SEQUENCE: 68

```
Xaa Thr Tyr Ser Leu His Cys Gly Pro Arg Thr Cys Val Val Arg Pro
1               5                   10                  15
Lys
```

<210> SEQ ID NO 69
<211> LENGTH: 34
<212> TYPE: PRT

```
<213> ORGANISM: Artificial
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Epsilon-aminocaproic acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 69

Xaa Thr Tyr Ser Leu His Cys Gly Pro Arg Thr Cys Val Val Arg Pro
1               5                   10                  15

Lys Xaa Thr Tyr Ser Leu His Cys Gly Pro Arg Thr Cys Val Val Arg
            20                  25                  30

Pro Lys
```

MODIFICATION OF PEPTIDES USING A BIS(THIOETHER)ARYLBRIDGE APPROACH

CROSS-REFERENCE TO RELATED APPLICATIONS

This application is a 371 National Phase of PCT/US2013/041650, filed May 17, 2013, which claims benefit of and priority to U.S. Ser. No. 61/649,000, filed on May 18, 2012, all of which are incorporated herein by reference in their entirety for all purposes.

STATEMENT OF GOVERNMENTAL SUPPORT

[Not Applicable]

BACKGROUND

For a long time, peptides were perceived as a poor drug candidates. They are prone to proteolytic degradation and rapid clearance in vivo through renal filtration. In addition, most of them are unable to maintain a well-defined three-dimensional structure, which is critical for their bioactivity, existing instead as a vast ensemble of conformational isomers (especially true for short, conformationally unrestricted analogues). Usually, they do not penetrate cells easily, hampering their use for intracellular targets. Over the years various strategies were employed to address these drawbacks, such as head-to-tail cyclization, lactam bridges, introduction of unusual-, α,α-disubstituted-, and (D)-amino acids, retro-inverso approach, lipidation/cholesterylation, multimerization, concatenation, development of targeted delivery systems, application of cell penetrating peptides (CPP), etc. Despite all shortcomings however, peptides possess advantages, chief among them is their practically unrestricted variability that can be tailored for specific needs. If relatively short, they may be also efficiently synthesized and purified using existing methodology. Due to various technological advances, new lead compounds may be relatively easy accessible through computer-aided rational design as well as randomization-based discovery methods utilizing solid-support-grafted peptide arrays and phage display. Recently, stapling has a prominent method in the development of peptide-drug candidates.

The peptide stapling strategy for stabilizing of peptide α-helices utilizes a ring-closing metathesis (RCM) reaction. The "staple" is efficiently created in a two-step process between strategically positioned olefin functionalized non-natural amino acid side chains. The first step, catalyzed by Grubbs catalyst, results in olefin containing bridge that is subsequently catalytically reduced to saturated hydrocarbon (alkane), effectively locking the peptide into a stable α-helix conformation. Such helix stabilization had been shown to dramatically increase the helicity, potency resistance to proteolytic degradation and cell permeability of α-helical peptides. However, the use of stapling technology is limited, especially in academic settings due to relatively high cost of olefin-containing amino acids.

SUMMARY

In various embodiments new methods for stabilization of peptides (e.g., α-helical peptides) are provided. In certain embodiments the methods provide an efficient protocol for simultaneous S-alkylation of two strategically placed cysteine residues within the peptide (see, e.g., FIG. 1). To this end di-halogeno-aryl-compounds (see, e.g., FIG. 2) can be used, resulting in the formation of bis(thioether)-Aryl-Bridge (tAB™). Reaction can be carried out "on resin" as well as "in solution" using fully deprotected peptides in organic solvents and/or in a water based mix. More than one tAB can be introduced in solution without the need for selective side chain protection of the Cys residues. Newly formed thioethers can be efficiently oxidized to respective sulfones (R—S—R→R—$SO_2$—R) allowing for additional points of modification/interaction with the respective target(s). Simultaneously, such modifications improve water solubility. To date, various tAB-ed peptides showed in vitro and in vivo bioactivity proving that the approach described herein provides an additional tool in development of peptide-based therapeutics.

In various aspects, the invention(s) contemplated herein may include, but need not be limited to, any one or more of the following embodiments:

Embodiment 1

A method of stabilizing a peptide, said method including: providing a peptide containing at least two S bearing residues; and reacting the peptide with a di-halogeno-aryl-compounds to form a bis(thioether)-Aryl-Bridge between said two residues.

Embodiment 2

A method of attaching two or more peptides to each other, said method including: providing two or more peptides containing at least one S bearing residue; and reacting the peptides with a di-halogeno-aryl-compounds to form a bis(thioether)-Aryl-Bridge between said residues at least two different peptides thereby attaching said peptides to each other through said bridge.

Embodiment 3

The method of embodiment 2, wherein said two or more peptides each have the same amino acid sequence.

Embodiment 4

The method of embodiment 2, wherein said two or more peptides comprise peptides having different amino acid sequences.

Embodiment 5

The peptide according to any one of embodiments 1-4, wherein said S bearing residues are selected from the group consisting of (L)Cys, (D)Cys, (L)homoCys, (D)homoCys, (L)Pen, and (D)Pen.

Embodiment 6

The peptide according to any one of embodiments 1-5, wherein said peptide is mutated/modified to introduce at least one of said S-bearing residues.

Embodiment 7

The method according to any one of embodiments 1-6, wherein said di-halogeno-aryl-compound has the formula $XCH_2$—Ar—$CH_2X$, where X is Cl, Br, or I.

Embodiment 8

The method of embodiment 7, wherein X is Cl.

Embodiment 9

The method of embodiment 7, wherein X is Br.

Embodiment 10

The method of embodiment 7, wherein X is I.

Embodiment 11

The method according to any one of embodiments 1-5, wherein said di-halogeno-aryl-compound has a formula found in FIG. 2 where any of the halogens illustrated therein can be Br, Cl, or I.

Embodiment 12

The method according to any one of embodiments 1-5, wherein said di-halogeno-aryl-compound has a formula found in FIG. 2.

Embodiment 13

The method according to any one of embodiments 1-5, wherein said di-halogeno-aryl-compound has a formula found in FIG. 2 where any of the halogens illustrated therein are all I.

Embodiment 14

The method according to any one of embodiments 1-5, wherein said di-halogeno-aryl-compound has a formula found in FIG. 2 where any of the halogens illustrated therein are all Cl.

Embodiment 15

The method according to any one of embodiments 1-14, wherein at least two bridges are formed.

Embodiment 16

The method according to any one of embodiments 1-15, wherein said peptide includes a helical domain.

Embodiment 17

The method according to any one of embodiments 1-15, wherein said peptide is a helical peptide.

Embodiment 18

The method according to any one of embodiments 16-17, wherein said helical domain or said helical peptide includes an alpha helix.

Embodiment 19

The method according to any one of embodiments 16-17, wherein said helical domain or said helical peptide includes a beta helix.

Embodiment 20

The method according to any one of embodiments 16-17, wherein said helical domain or said helical peptide includes a mixed alpha and beta helix.

Embodiment 21

The method according to any one of embodiments 16-17, wherein said helical domain or said helical peptide includes a class A helix.

Embodiment 22

The method according to any one of embodiments 1-21, wherein said peptide ranges in length up to about 100 amino acids, or up to about 75 amino acids, or up to about 50 amino acids, or up to about 40 amino acids, or up to about 35 amino acids, or up to about 30 amino acids, or up to about 25 amino acids, or up to about 20 amino acids, or up to about 18 amino acids, or up to about 15 amino acids.

Embodiment 23

The method according to any one of embodiments 1-21, wherein said peptide is a peptide found in any one of Tables 1-5.

Embodiment 24

A peptide stabilized with at least one bis(thioether)aryl bridge between two S-bearing residues within said peptide.

Embodiment 25

The peptide of embodiment 24, wherein said S bearing residues are selected from the group consisting of (L)Cys, (D)Cys, (L)homoCys, (D)homoCys, (L)Pen, and (D)Pen.

Embodiment 26

The peptide according to any one of embodiments 24-25, wherein said peptide is mutated/modified to introduce at least one of said S-bearing residues.

Embodiment 27 the peptide according to any one of embodiments 24-26, wherein said one bis(thioether)aryl bridge is introduced into said peptide by reacting a peptide lacking said bridge with a di-halogeno-aryl-compounds to form a bis(thioether)-Aryl-Bridge between said two residues.

Embodiment 28

The peptide of embodiment 27, wherein said di-halogeno-aryl-compound has the formula $XCH_2$—Ar—$CH_2X$, where X is Cl, Br, or I.

Embodiment 29

The peptide of embodiment 28, wherein X is Cl.

Embodiment 30

The peptide of embodiment 28, wherein X is Br.

Embodiment 31

The peptide of embodiment 28, wherein X is I.

Embodiment 32

The peptide of embodiment 28, wherein said di-halogeno-aryl-compound has a formula found in FIG. 2 where any of the halogens illustrated therein can be Br, Cl, or I.

Embodiment 33

The peptide of embodiment 28, wherein said di-halogeno-aryl-compound has a formula found in FIG. 2.

Embodiment 34

The peptide according to any one of embodiments 24-33, wherein said peptide includes at least two bis(thioether)-aryl-bridges.

Embodiment 35

The peptide according to any one of embodiments 24-34, wherein said peptide includes a helical domain.

Embodiment 36

The peptide according to any one of embodiments 24-34, wherein said peptide is a helical peptide.

Embodiment 37

The peptide according to any one of embodiments 35-36, wherein said helical domain or said helical peptide includes an alpha helix.

Embodiment 38

The peptide according to any one of embodiments 35-36, wherein said helical domain or said helical peptide includes a beta helix.

Embodiment 39

The peptide according to any one of embodiments 35-36, wherein said helical domain or said helical peptide includes a mixed alpha and beta helix.

Embodiment 40

The peptide according to any one of embodiments 35-36, wherein said helical domain or said helical peptide includes a class A helix.

Embodiment 41

The peptide according to any one of embodiments 24-30, wherein said peptide ranges in length up to about 100 amino acids, or up to about 75 amino acids, or up to about 50 amino acids, or up to about 40 amino acids, or up to about 35 amino acids, or up to about 30 amino acids, or up to about 25 amino acids, or up to about 20 amino acids, or up to about 18 amino acids, or up to about 15 amino acids.

Embodiment 42

The of embodiment 24, wherein said peptide is a peptide found in any one of Tables 1-5.

Embodiment 43

The peptide according to any one of embodiments 24-42, wherein said peptide shows improved stability in solution as compared to the same peptide lacking said bridge(s).

Embodiment 44

The peptide according to any one of embodiments 24-42, wherein said peptide shows increased serum half-life in vivo as compared to the same peptide lacking said bridge(s).

Embodiment 45

The peptide according to any one of embodiments 24-42, wherein said peptide shows increased bioavailability in vivo as compared to the same peptide lacking said bridge(s).

Embodiment 46

A pharmaceutical formulation including: a therapeutic peptide modified with a bis(thioether)-Aryl-Bridge (tAB™); and a pharmaceutically acceptable excipient.

Embodiment 47

The formulation of embodiment 46, wherein said peptide includes a peptide according to any one of embodiments 24-45.

Embodiment 48

The formulation of embodiment 46, wherein said peptide includes a peptide selected from the group consisting of (15-29)p53, ArB14Ao, ArB14Bo, ArB14C-Ch/CLB, ArB14Co, ArB14Co-AZT, ArB14Co-Ch, ArB14Co-Ch/CLB, ArB14Co-CLB, ArB14Co-MTX, ArB14Co-TFA, ArB14Co-TFAo, ArB14Dm, ArB14Dmx, ArB14Em, ArB14Emx, ArB14o, ArB15Am, ArB15Bm, ArB15Cp, ArB15Dp, ArB15Eb, ArB15F/G0/Nic, ArB15F/GNicr, ArB15F/GNict, ArB15F/Gr, ArB15F/Gt, ArB15FNico, ArB15Fo, ArB15Gm, ArB15GNicm, ArB17Ac, ArB17Bc, ArB18Ac, ArB18Bc, ArB-4Fo, ArB-4Fox, ArB-4Fr, ArB-Mim, DpV13, DpV13ST, DpV13STOX, Mix, PalHemArB, PalHemArB2, PMI_M, and PMI_N8A.

Embodiment 49

The formulation of embodiment 46, wherein said peptide includes a peptide selected from the group consisting of SMAC1, SMAC2, SMAC3, SMAC4, SMAC5, SMAC6, SMAC7, SMAC8, SMAC9, SMAC10, SMAC11, SMAC12, SMAC13, SMAC14, SMAC14-2X, SMAC14-3X, SMAC15, SMAC16, SMAC17, SMAC17-2X, SMAC17-3X, SMAC18, SMAC19, and the like.

Embodiment 50

The formulation of embodiment 46, wherein said peptide includes a peptide selected from the group consisting growth hormone, growth hormone releasing hormone (GHRH), alpha interferon, beta interferon, gamma interferon, IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, IL-36, etc.), porcine insulin, bovine insulin, human insulin, insulin-like growth factor-1 (IGF-1), insulin-like growth factor-2 (IGF2, somatostatin), heparin, heparinoids, dermatans, chondroitins, calcitonin, influenza antigen, hepatitis A antigen, hepatitis B antigen, hepatitis C antigen, HPV antigen, oxytocin, leutinizing-hormone-releasing hormone (LHRH), follicle stimulating hormone (FSH); glucocerebrosidase, thrombopoietin; filgrastim, prostaglandins, vasopressin, cromolyn sodium vancomycin, desferrioxamine (DFO), parathyroid hormone (PTH), ecallantide (plasma kallikrein inhibitor), telavancin (antibacterial agent), romidepsin (HDAC inhibitor), liraglutide (GLP-1 receptor agonist), boceprevir (NS3/4A protease inhibitor), telaprevir (NS3/4A protease inhibitor), icatibant (bradykinin B2 receptor antagonist), and antimicrobial peptides.

Embodiment 51

The formulation according to any one of embodiments 46-50, wherein said formulation is a unit dosage formulation.

Embodiment 52

The formulation according to any one of embodiments 46-51, wherein said formulation is a sterile formulation.

Embodiment 53

The formulation according to any one of embodiments 46-52, wherein the formulation is for administration via a route selected from the group consisting of isophoretic delivery, transdermal delivery, aerosol administration, administration via inhalation, oral administration, intravenous administration, and rectal administration.

DEFINITIONS

The terms "polypeptide", "peptide" and "protein" are used interchangeably herein to refer to a polymer of amino acid residues. Thus, the methods described herein are considered applicable to both "short" peptides and to long (longer) proteins. In certain embodiments the peptide ranges in length from about 2, 3, 4, 5, 7, 9, 10, or 11 residues to about 200, 150, 100, 80, 60, 50, 45, 40, 45, 30, 25, or 20 residues. In certain embodiments the peptide ranges in length from about 8, 9, 10, 11, or 12 residues to about 15, 20, 25, 30, 35, 40, 45, or 50 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, phosphonamide, carbomate, hydroxylate, and the like (see, e.g., Spatola, (1983) *Chem. Biochem. Amino Acids and Proteins* 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "residue" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. These modified amino acids are illustrative and not intended to be limiting.

"β-peptides" comprise of "β amino acids", which have their amino group bonded to the β carbon rather than the α-carbon as in the 20 standard biological amino acids. The only commonly naturally occurring β amino acid is β-alanine.

Peptoids, or N-substituted glycines, are a specific subclass of peptidomimetics. They are closely related to their natural peptide counterparts, but differ chemically in that their side chains are appended to nitrogen atoms along the molecule's backbone, rather than to the α-carbons (as they are in natural amino acids).

Where an amino acid sequence is provided herein, L-, D-, or beta amino acid versions of the sequence are also contemplated as well as retro, inversion, and retro-inversion isoforms. In addition, conservative substitutions (e.g., in the binding peptide, and/or antimicrobial peptide, and/or linker peptide). Non-protein backbones, such as PEG, alkane, ethylene bridged, ester backbones, and other backbones are also contemplated. Also fragments ranging in length from about 5, 6, 7, 8, 9, 10, 11, 12, 13, 14, 15, 16, 17, 18, 19, 20, 21, 22, 23, 24, or 25 amino acids up to the full length minus one amino acid of the peptide are contemplated where the fragment retains at least 50%, preferably at least 60% 70% or 80%, more preferably at least 90%, 95%, 98%, 99%, or at least 100% of the biological activity of the full length peptide are contemplated.

The term "an amphipathic helical peptide" refers to a peptide comprising at least one amphipathic helix (amphipathic helical domain). Certain amphipathic helical peptides of this invention can comprise two or more (e.g., 3, 4, 5, etc.) amphipathic helices.

The term "class A amphipathic helix" refers to a protein structure that forms an α-helix producing a segregation of a polar and nonpolar faces with the positively charged residues residing at the polar-nonpolar interface and the negatively charged residues residing at the center of the polar face (see, e.g., Segrest et al. (1990) *Proteins: Structure, Function, and Genetics* 8: 103-117).

14Co:11.2±1.2; 14Bo:10.7±0.7; 14Co-CLB:7.5±1.1; 14Co-MTX:6.9±0.4; 14Co-AZT:30.2±2.5. Bottom panel: In vivo data from subcutaneous engraftment mouse model (HCT116/SCID). Administration of ArB14Co results in ~14.6 days of tumor growth delay.

Figure 4:
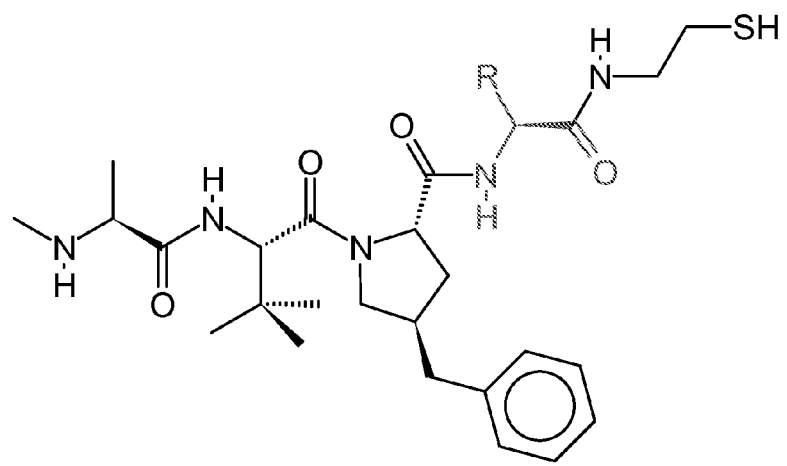

FIG. 4 illustrates the structure of members of SMAC library.

Figure 5A:
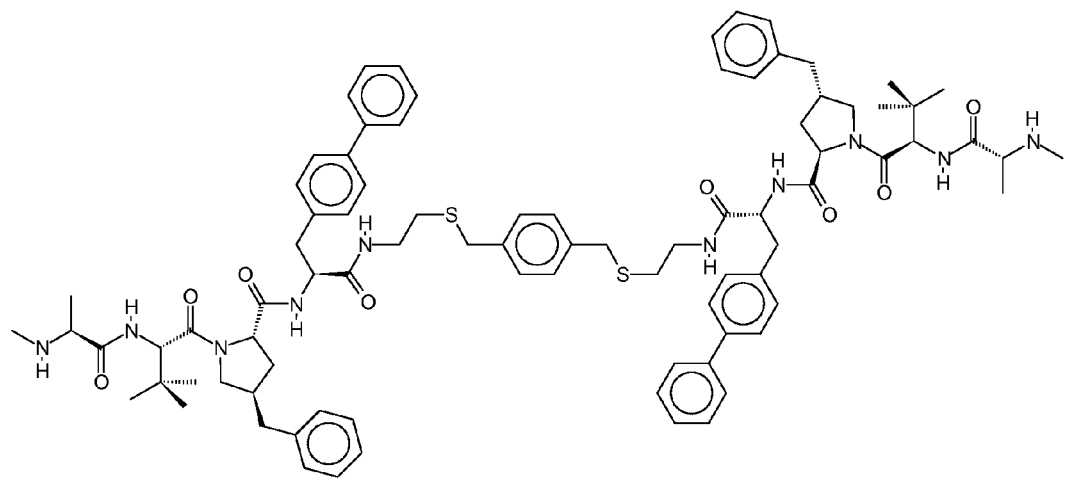
Figure 5B:
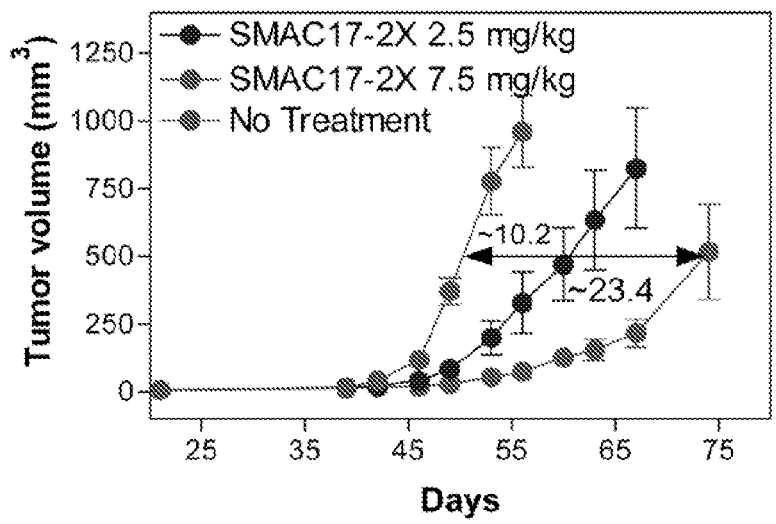

FIG. 5A shows the structure of SMAC17-2X and FIG. 5B shows in vivo results from subcutaneous engraftment mouse model (MDA-MB-231/SCID).

Figure 6A:
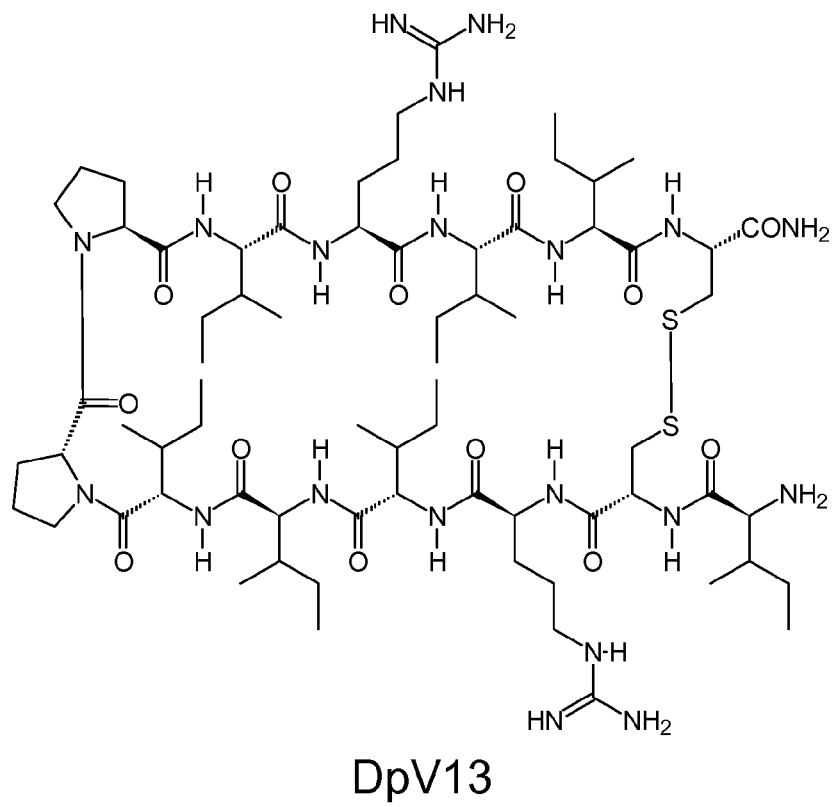
Figure 6B:
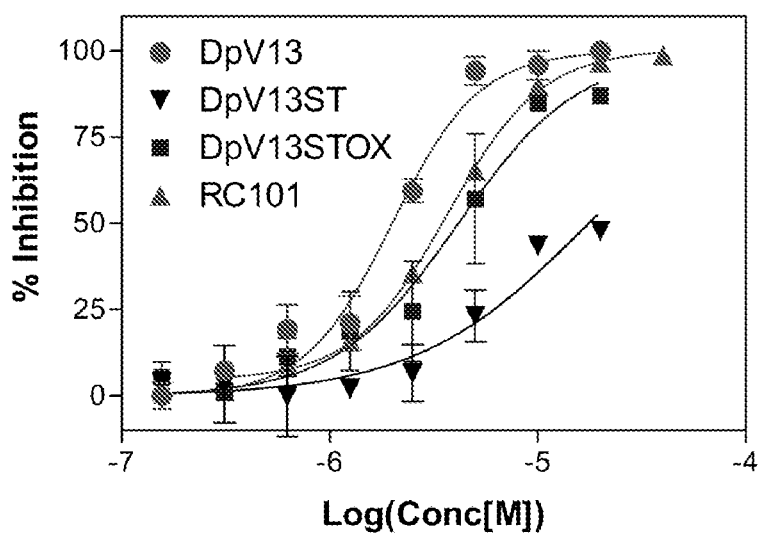

FIG. 6A shows structures of DpV13, DpV13ST, and dpV13STOX. FIG. 6B shows their anti-HIV activity in dose response experiments using TZMB1 assay and DpV derivatives. Θ-defensin RC101 serves as a positive control.

Figure 7A:
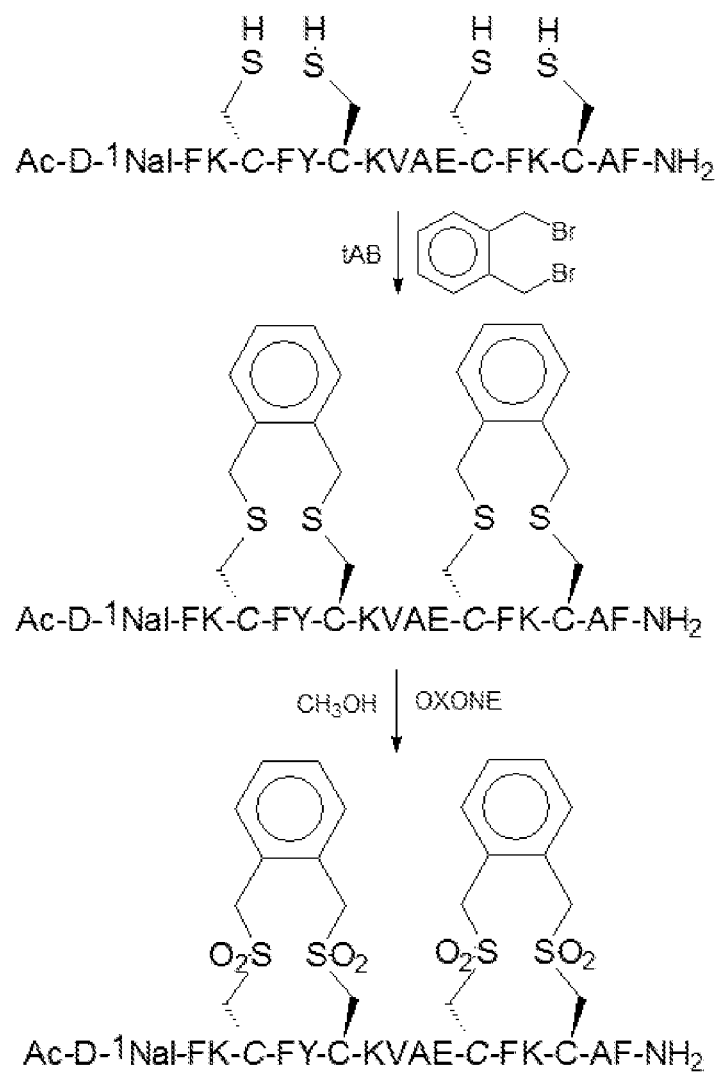
Figure 7B:
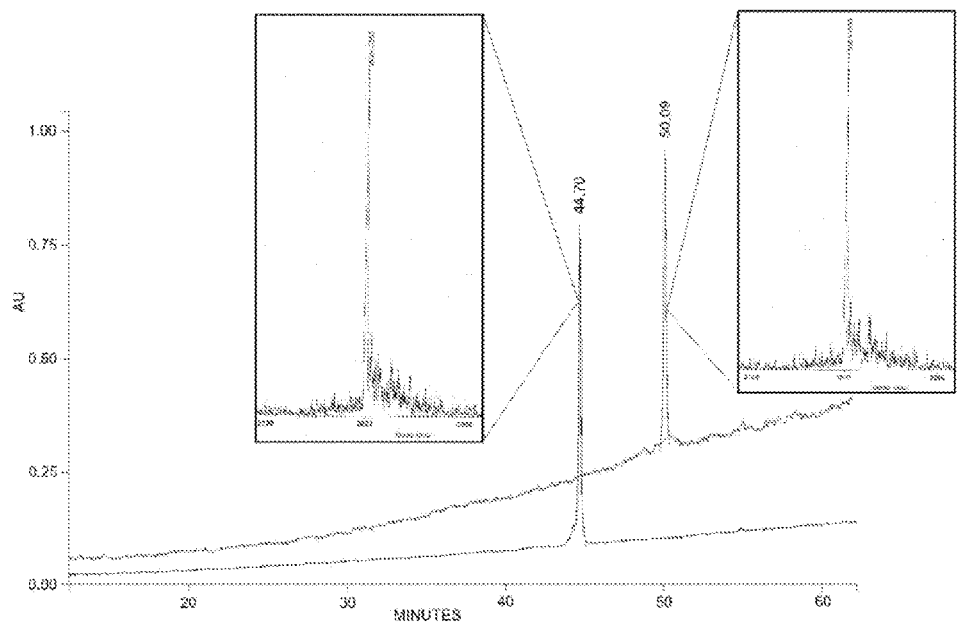

FIG. 7A shows an assembly scheme for L4F double tAB-ed 4F derivatives ArB-4Fo, ArB-4Fox (SEQ ID NO:1). FIG. 7B: Analytical HPLC profiles and MS spectra for double tAB-ed 4F derivative and its oxidized counterpart.

Figure 8:
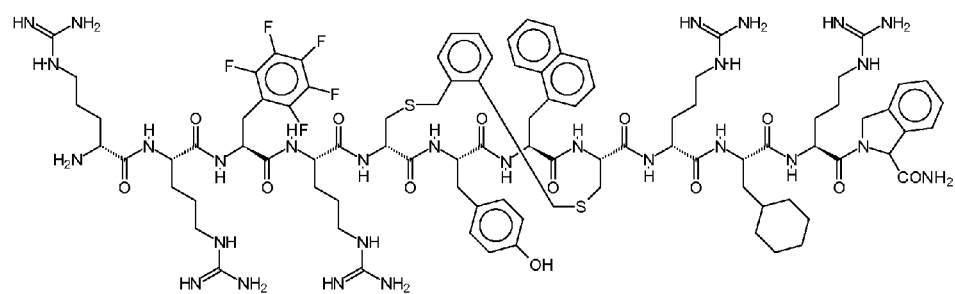

FIG. 8 illustrates the structure of ArB14Co (SEQ ID NO:7).

Figure 9:
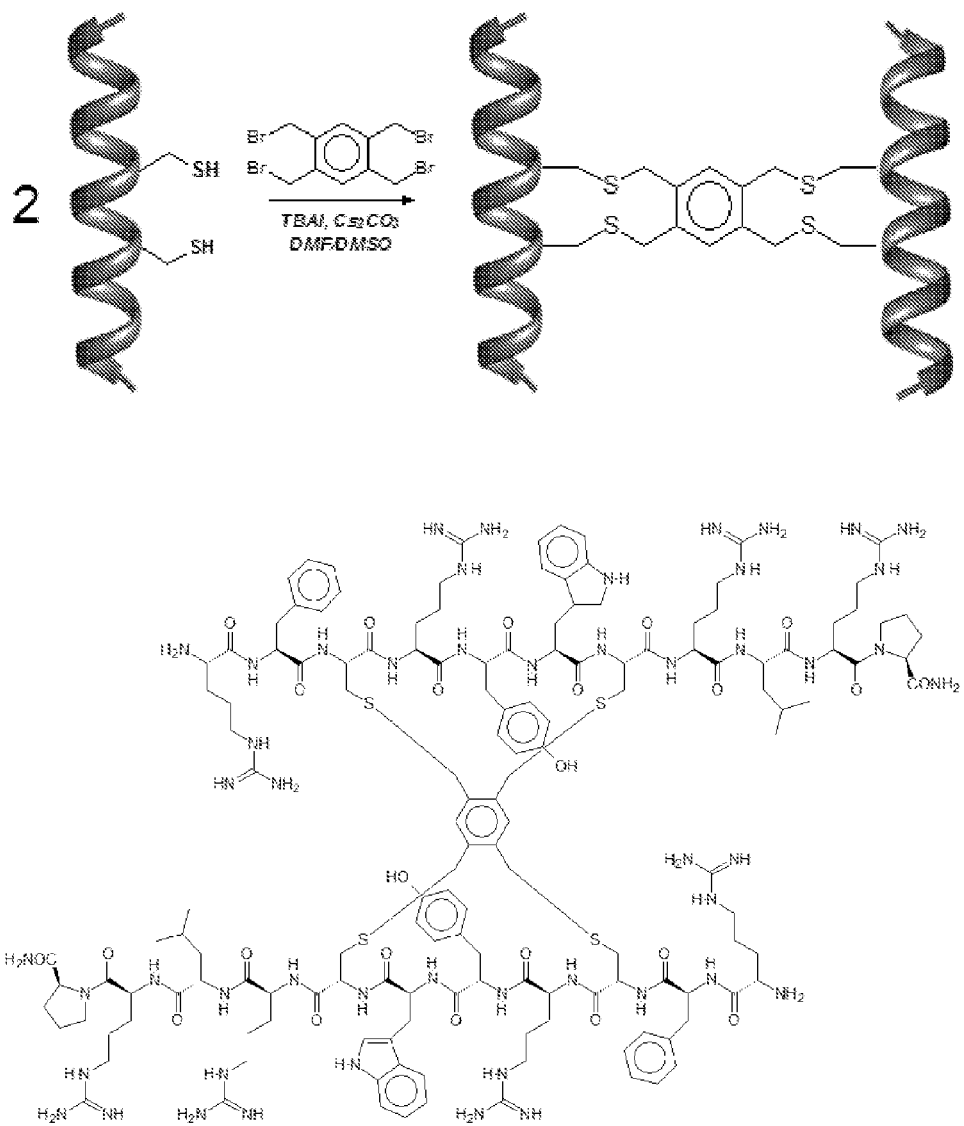

FIG. 9 shows a schematic representation and one of four possible structures of ArB15F/Gt (SEQ ID NO:28).

Figure 10:
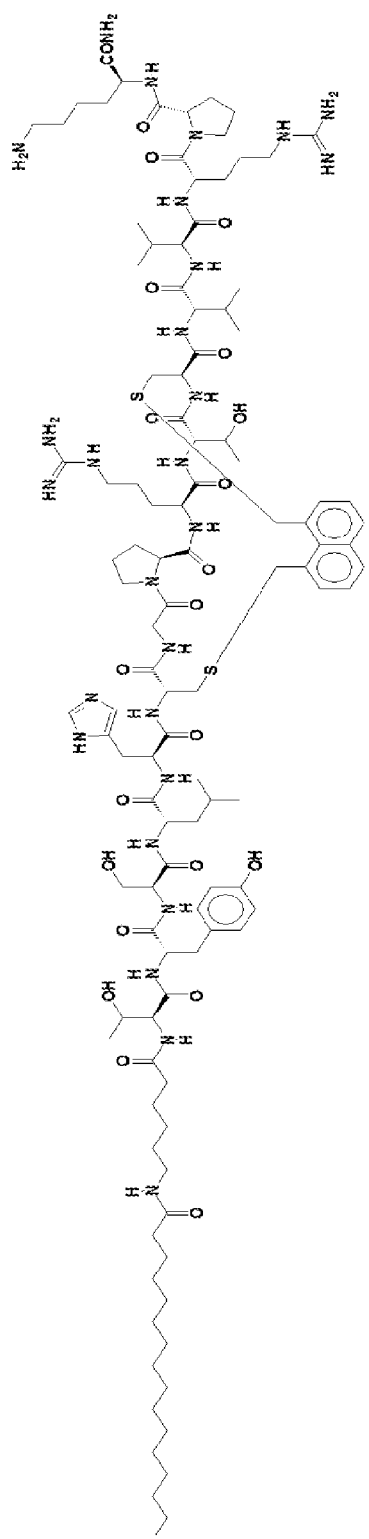

FIG. 10 illustrates the structure of PalHemArB (SEQ ID NO:43).

Figure 11:
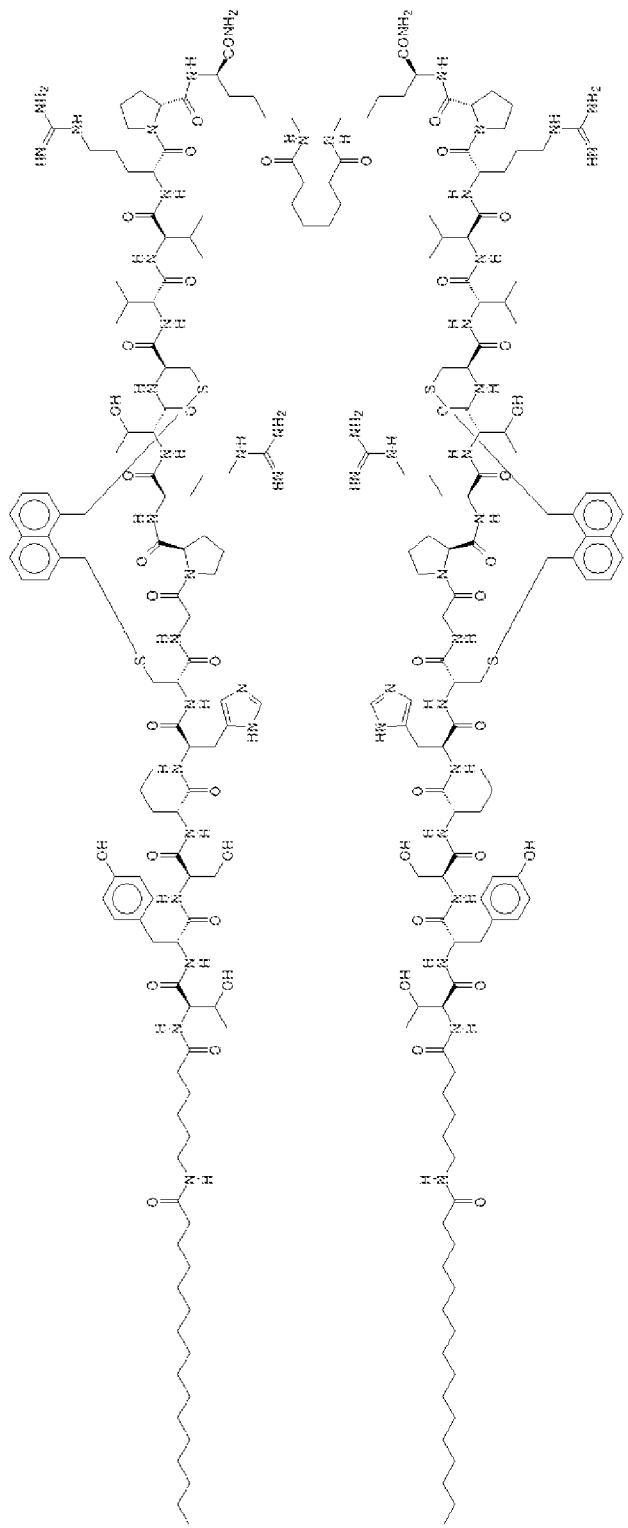

FIG. 11 illustrates the structure of PalHemArB2 (SEQ ID NO:44).

Figure 12:
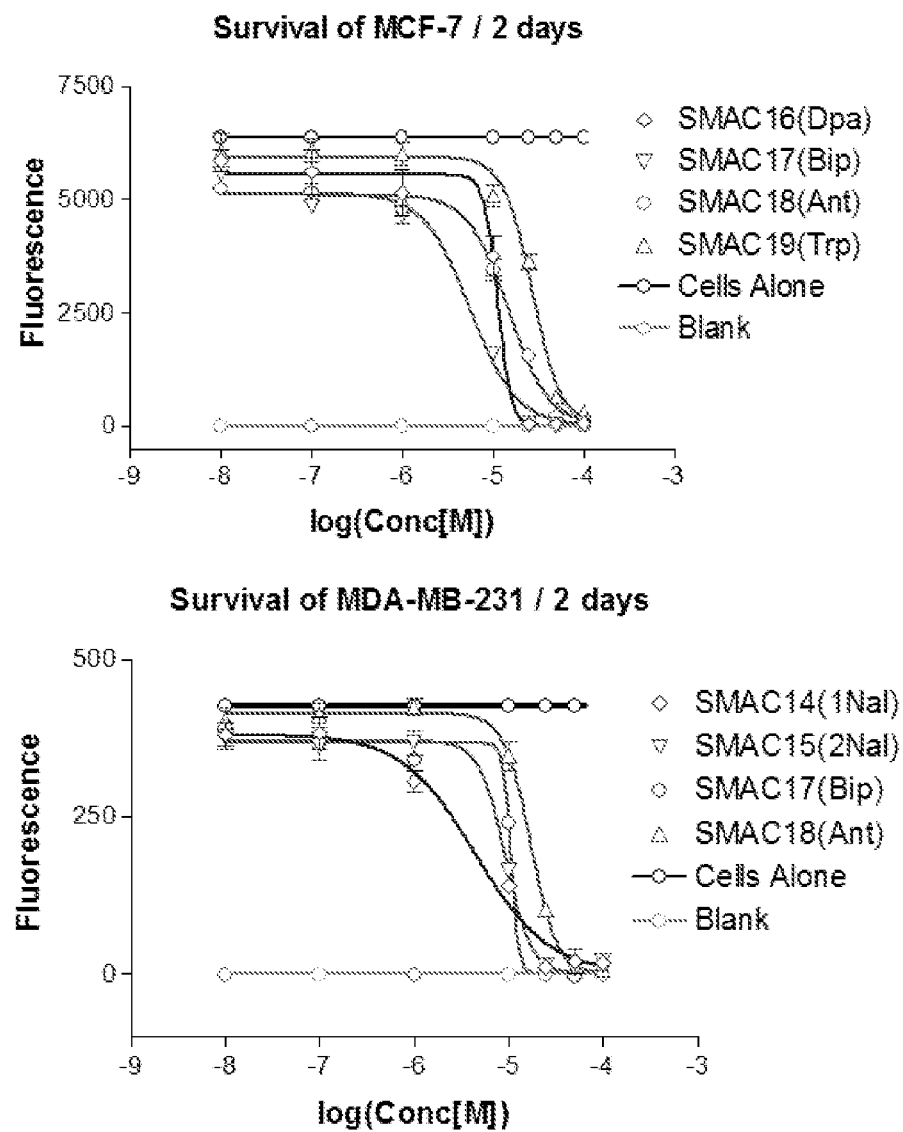

FIG. 12 shows examples of cell viability assay experiments for Smac analogues.

DETAILED DESCRIPTION

In our work on various anticancer and antiviral compounds we realized that use of stapling technology may be limited, especially in academic settings due to relatively high cost of olefin-containing amino acids. Therefore we started looking for alternatives with two principles in mind: all compounds necessary must be (1) commercially available and (2) inexpensive.

In recent years stapling of peptides emerged as a leading strategy in the development of novel peptide-based drug candidates. Since a pivotal Blackwell & Grubbs paper (*Angew. Chem. Int. Ed.* 1998:37,3281), numerous studies were carried out utilizing this approach yielding potent bioactive compounds as well as resulting in the foundation of a specialized company, Aileron Therapeutics.

This discovery pertains to chemical modification of peptides to improve stability (e.g., to increase serum half-life, and/or bioavailability). It is believed that such stabilization improves the utility of peptides as potential drugs. The methods described herein provide an alternative to the typical "peptide stapling technology". Moreover, the methods described herein offer certain advantages including, but not limited to, the possibility of performing "thiobridging" in water based solutions and using unprotected peptides (both of which are highly problematic in peptide stapling methodologies).

The approaches described herein do not require the use of unusual and expensive amino acids. Potential applications include, but are not limited to all fields and human diseases where peptides are being used as bioactive agents. Data are presented win which the technology yielded potent novel anti-cancer and anti-viral compounds.

Figure 1:
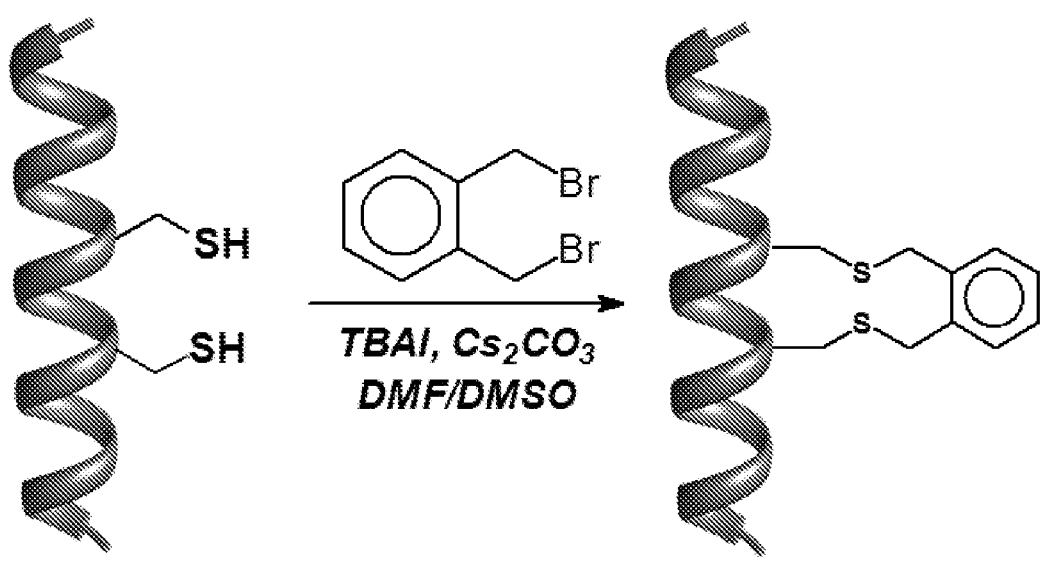
FIG. 1 illustrates one example of bis(thioether)-Aryl-Bridge (tAB™) approach to peptide stabilization.

One illustrative approach for stabilization of peptides (e.g., α-helical peptides) provides an efficient protocol for simultaneous S-alkylation of two strategically placed cysteine residues within the peptide (see, e.g., FIG. 1). To this end di-halogeno-aryl-compounds (see, e.g., FIG. 2) can be used, resulting in the formation of bis(thioether)-Aryl-Bridge (tAB™). Reaction can be carried out "on resin" as well as "in solution" using fully deprotected peptides in organic solvents and/or in a water based mix. More than one tAB can be introduced in solution without the need for selective side chain protection of the Cys residues. Newly formed thioethers can be efficiently oxidized to respective sulfones (R—S—R→R—SO$_2$—R) allowing for additional points of modification/interaction with the respective target(s). Simultaneously, such modifications improve water solubility. To date, some of our tAB-ed peptides showed in vitro and in vivo bioactivity proving that our approach may provide additional tool in development of peptide-based therapeutics.

As indicated above, generally, bis(thioether)arylbridging (tAB-ing) can be performed either on the solid support on in solution. In one illustrative, but non-limiting "in solution" protocol, peptide (1 eq) containing 2 properly placed cysteines (or similar —SH containing amino acids) is mixed in a solution of DMF (N,N-dimethylformamide) and DMSO (dimethylsulfoxide) (1:1 ratio, concentration of peptide: 0.5-1 mg/mL) with the bis(halogenomethyl)aryl compound (XCH$_2$—Ar—CH$_2$X, where X=Cl, Br, I) in the presence of cesium carbonate (Cs$_2$CO$_3$, 10 eq) and tetrabutylammonium iodide (TBAI, 1 eq). Reaction can be monitored by HPLC/mass spectrometry.

In one illustrative, but non-limiting "on the solid support" protocol: After assembly of the peptide, the final protecting group (e.g., Fmoc) is removed and Cys residues are deprotected. The deprotection protocol depends on the type of Cys derivatives that are used. For Cys(Trt): 2% trifluoroacetic acid (TFA), 2% triisopropyl silane (TIS) in dichloromethane (DCM) (3×10 min). Then the peptide is washed with DMF and bis(thioether)aryl bridging performed on resin as described above, except the reaction is performed in DMF without DMSO.

The following bis(halogenomethyl) compounds have been successfully employed:
1) 1,2-bis(bromomethyl)benzene;
2) 1,3-bis(bromomethyl)benzene;
3) 1,4-bis(bromomethyl)benzene;
4) 1-(bromomethyl)-3-[3-(bromomethyl)benzyl]benzene,
5) 1-(chloromethyl)-4-[4-(chloromethyl)phenoxy]benzene; and
6) 1,2-bis(bromomethyl)naphthalene.

Figure 2:
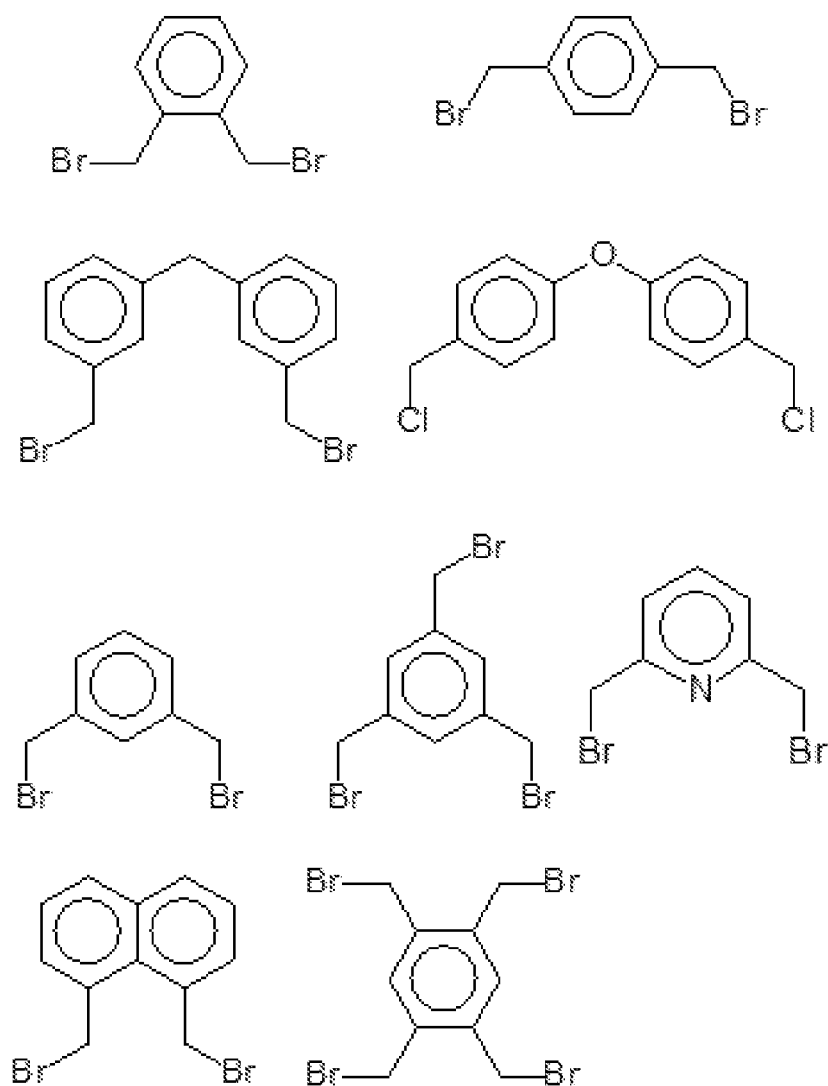
FIG. 2 illustrates some dihalogeno-aromatic components that can be used to create tAB peptide.
Figure 3:
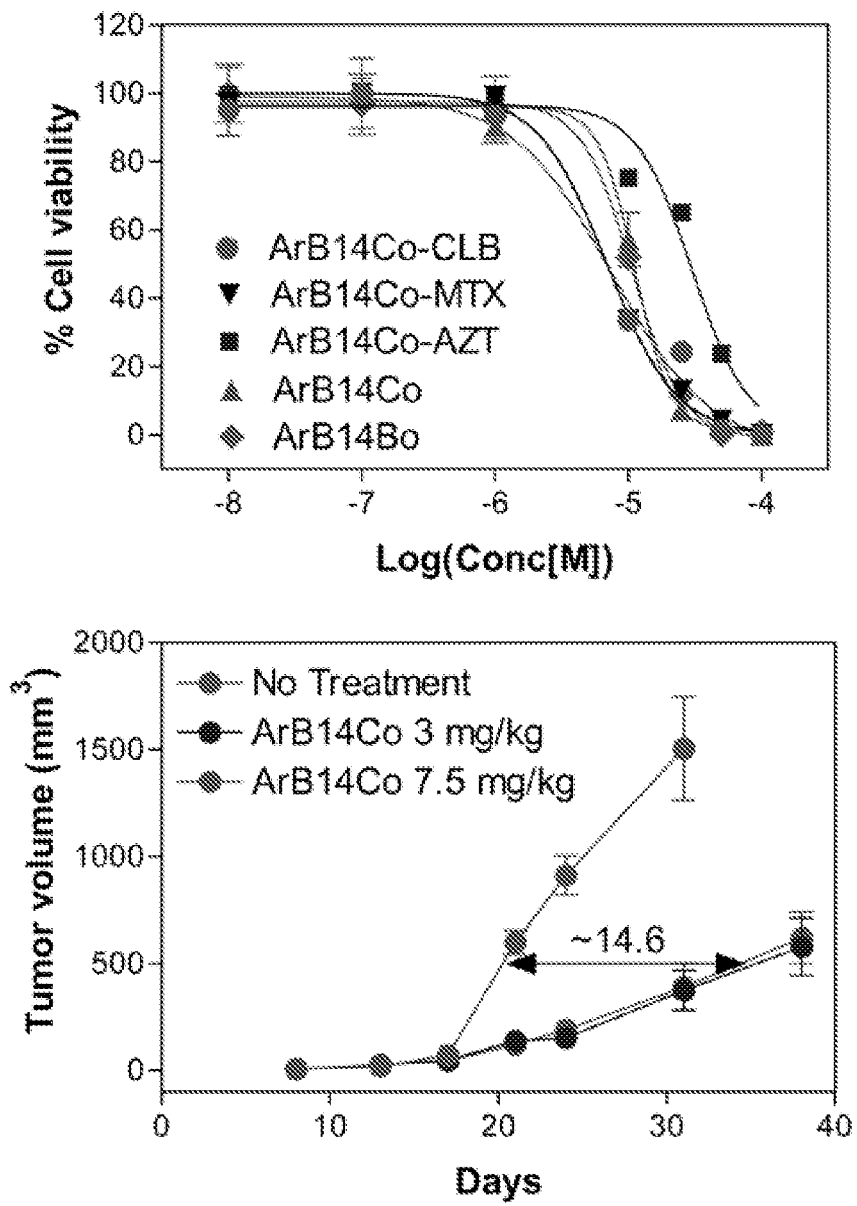
FIG. 3 Top panel: Cell viability data for selected compounds. Compounds possess following $EC_{50}$ values (µM)

However the bis(halogenomethyl) compounds need not be limited to these or to the compounds shown in FIG. 2. Using the teachings provided herein, other bis(halogenomethyl) compounds will be available to one of skill in the art.

In certain embodiments multimerization is performed in solution as described above, using peptide containing one —SH group (1 eq) per each XCH$_2$-group of aryl compound. For dimerization as an aryl compound we used 1,4-bis(bromomethyl)benzene, and for trimerization we used 1,3,5-tris(bromomethyl)benzene. For the dimerization of two helical peptides we used 1,2,4,5-tetrakis(bromomethyl)benzene, however the reaction yields mixtures of variously dimerized compounds (4 possible combinations) and yields are low.

In certain illustrative, but non-limiting embodiments oxidation of thioethers to sulfones was performed using OXONE (Sigma-Aldrich, KHSO$_5$*0.5KHSO$_4$*0.5K$_2$SO$_4$) in methyl alcohol-water mix (3:1) using 3 eq of oxone per each thioether group. Reaction was carried out in room temperature for 3 h. Subsequently solution was freeze-dried and purified using reverse phase HPLC (RP-HPLC). DpV13ST (see, FIG. 6A) was synthesized in solution as described above using 1,2-bis(bromomethyl)benzene as an aryl compound. DpV13STOX was synthesized from DpV13ST using oxidation protocol described above.

ArB-4Fo (tAB-ed analogue of L4F) (see, FIG. 7 A) was synthesized in solution from purified reduced peptide (1 eq) and 1,2-bis(bromomethyl)benzene (2 eq). ArB-4Fox was synthesized from ArB-4Fo by oxidation using OXONE protocol (see above).

Synthesis of PalHemArB (Hematide analogue). Reduced peptide was synthesized on the solid support, cleaved and purified on RP-HPLC. Reduced peptide was tAB-ed using in solution protocol and 1,8-bis(bromomethyl)naphthalene. Monomer was subsequently dimerized overnight using bis (N-hydroxysuccinimide ester) of suberic acid (Sigma-Aldrich) in DMSO (10 mg/mL) and in the presence of N-methyl-morpholine (NMM, 10 eq). Dimer was purified on RP-HPLC.

By way of illustration, the examples described herein illustrate two types of potential anticancer agents:
1) Smac analogues (see, e.g., Nat Rev Drug Discov. 2012: 11(2):109-24, and for Smac dimers see J Med Chem. 2012; 55(1):106-14 and J. Med. Chem. 2011:54,3306); and
2) The dual-specific antagonist of p53-MDM2/MDMX (see PNAS 2009:106,4665; J. Mol. Biol. 2010:398,200 & Proc. Natl. Acad. Sci. U.S.A. 2010:107,14321).

In addition also shown in the examples are:
3) Antiviral derivatives of Diprovirins (J. Immunol. 2012: 188,2759; and Int J Pept Res Ther, 2011; 17(4):325-336);
4) Analogues of L4F (apoA-I-mimetic peptide, Curr Opin Investig Drugs. 2010:11(9):989-96, Curr Atheroscler Rep. 2009:11(1):52-7, Proc Natl Acad Sci USA. 2010:107(46): 19997-20002); and
5) Hematide (peginesatide) analogue (erythropoietin (EPO) mimetic peptide. Hematide is approved by the FDA (see, e.g., *Drug Chem Toxicol.* 2010:33(1):28-37, N Engl J Med. 2009 Nov. 5; 361(19):1848-55, Rapid Commun Mass Spectrom. 2011:25(15):2115-23, review: Expert Rev Hematol. 2009:2(4):377-83).

As indicated above, the modified peptides described herein (e.g., therapeutic peptide(s) modified with a bis (thioether)-aryl-bridge (tAB™) can show improved stability and/or bioavailability. Accordingly in various embodiments, the modification (e.g., bis(thioether)-aryl-bridge modification) of essentially any therapeutic peptide is contemplated as are pharmaceutical formulations thereof.

A wide variety of therapeutic peptides are known to those of skill in the art and can be modified according to the methods described herein. Such peptides include, but are not limited to, growth hormone (e.g., isolated and/or human, porcine, or bovine growth hormones), natural, synthetic, or recombinant growth hormone releasing hormones (GHRH), interferons (e.g., alpha, beta, and gamma interferon), interleukins (e.g., IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, IL-36, etc.), natural, synthetic or recombinant insulin (e.g., porcine, bovine, human insulins), insulin-like growth factor-1 (IGF-1), insulin-like growth factor-2 (IGF2, somatostatin), heparin, heparinoids, dermatans, chondroitins, calcitonin (e.g., natural, synthetic, or recombinant salmon, porcine, eel, chicken, and human calcitonin), antigens (e.g., influenza antigen, hepatitis A, B, C antigen, HPV antigen, etc.), antibodies (polyclonal and monoclonal) (e.g., HERCEPTIN®, RITUXAN®, AVASTIN®, ERBITUX®, etc.), oxytocin, leutinizing-hormone-releasing hormone (LHRH), follicle stimulating hormone (FSH); glucocerebrosidase, thrombopoietin; filgrastim; prostaglandins; vasopressin; cromolyn sodium (e.g., sodium or disodium chromoglycate), vancomycin, desferrioxamine (DFO); parathyroid hormone (PTH) including its fragments, ecallantide (plasma kallikrein inhibitor), telavancin (antibacterial agent), romidepsin (HDAC inhibitor), liraglutide (GLP-1 receptor agonist), boceprevir (NS3/4A protease inhibitor), telaprevir (NS3/4A protease inhibitor), icatibant (bradykinin B2 receptor antagonist), antimicrobials (e.g., anti-bacterial agents, including anti-fungal agents, etc.), and the like. In addition, the therapeutic peptides include analogs, fragments, mimetics or modified derivatives of these compounds (e.g., polyethylene glycol (PEG)-modified derivatives, glycosylated derivatives, etc.), or any combination thereof.

In certain preferred embodiments, the therapeutic peptides are peptides that ameliorate one or more symptoms of a pathology associated with an inflammatory response (e.g., atherosclerosis). Such peptides include, but are not limited to ApoA-I (natural, synthetic, recombinant), ApoA-I milano, (natural, synthetic, recombinant), apolipoprotein M, 18A, and related peptides (see, e.g., U.S. Pat. No. 4,643,988, U.S. Pat. No. 6,037,323, and PCT Publication WO 97/36927 all of which are incorporated herein by reference).

As indicated above, in certain embodiments, pharmaceutical formulations comprising one or more a therapeutic peptides modified with a bis(thioether)-Aryl-Bridge (tAB™) ("modified peptides) are contemplated. In certain embodiments, the modified peptides comprise one or more modified peptides found in any one of Tables 1-5. In certain embodiments the modified peptides are provided as a pharmaceutical formulation comprising the modified peptide(s) in combination with a pharmaceutically acceptable carrier or excipient. The modified peptide(s) can be administered in the "native" form or, if desired, in the form of salts, esters, amides, prodrugs, derivatives, and the like, provided the salt, ester, amide, prodrug or derivative is suitable pharmacologically, e.g., effective in the present method(s). Salts, esters, amides, prodrugs and other derivatives of the modified peptide(s) can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, a pharmaceutically acceptable salt can be prepared for any compound described herein having a functionality capable of forming a salt, such as the carboxylic acid or tetrazole functionality of the compounds described herein. A pharmaceutically acceptable salt is any salt which retains the activity of the parent compound and does not impart any deleterious or untoward effect on the subject to which it is administered and in the context in which it is administered.

In various embodiments, pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically modified peptides as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the modified peptides herein include halide salts, such as may be prepared using hydrochloric or hydrobromic acids. Conversely, preparation of basic salts of the modified peptides described herein are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

In various embodiments, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the modified peptide. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the modified peptides identified herein are useful for parenteral, topical, oral, nasal (or otherwise inhaled), rectal, or local administration, such as by aerosol or transdermally, for prophylactic and/or therapeutic treatment of one or more of the pathologies/indications as understood by one of skill in the art.

The modified peptides described herein can be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the modified peptide(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the modified peptides, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g., calcium carbonate, carboxymethylcellulose calcium, sodium starch glycollate, crospovidone etc.), a binder (e.g., alphastarch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the modified peptide(s) and the resulting composition is compressed. Where necessary the compressed product is coated, e.g., using known methods for masking the taste, and/or for enteric dissolution, and/or for sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the modified peptide(s) and on the particular physio-chemical characteristics of the modified peptide(s).

In certain embodiments, the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectable, implantable sustained-release formulations, mucoadherent films, topical varnishes, lipid complexes, etc.

Pharmaceutical compositions comprising the modified peptide(s) can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the modified peptides into preparations that can be used pharmaceutically. Proper formulation is dependent upon the route of administration chosen.

For topical administration the modified peptides described herein can be formulated as solutions, gels, ointments, creams, suspensions, and the like as are well-known in the art. Systemic formulations include, but are not limited to, those designed for administration by injection, e.g., subcutaneous, intravenous, intramuscular, intrathecal or intraperitoneal injection, as well as those designed for transdermal, transmucosal oral or pulmonary administration. For injection, the modified peptides described herein can be formulated in aqueous solutions, preferably in physiologically compatible buffers such as Hanks solution, Ringer's solution, or physiological saline buffer and/or in certain emulsion formulations. The solution can contain formulatory agents such as suspending, stabilizing and/or dispersing agents. In certain embodiments, the modified peptide(s) can be provided in powder form for constitution with a suitable vehicle, e.g., sterile pyrogen-free water, before use. For transmucosal administration, penetrants appropriate to the barrier to be permeated can be used in the formulation. Such penetrants are generally known in the art.

For oral administration, the compounds can be readily formulated by combining the modified peptide(s) with pharmaceutically acceptable carriers well known in the art. Such carriers enable the modified peptides to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the modified peptide(s) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In various embodiments, the modified peptide(s) can be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that may be used to protect and deliver pharmaceutically active compounds. Certain organic solvents such as dimethylsulfoxide also can be employed, although usually at the cost of greater toxicity. Additionally, the compounds may be delivered using a sustained-release system, such as semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

In certain embodiments, the modified peptides described herein are administered orally. This is readily accomplished by the use of tablets, caplets, lozenges, liquids, and the like.

In certain embodiments, the modified peptides described herein are administered systemically (e.g., orally, or as an injectable) in accordance with standard methods well known to those of skill in the art. In other embodiments, the agents can also be delivered through the skin using conventional transdermal drug delivery systems, e.g., transdermal "patches" wherein the modified peptide(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the modified peptide(s) and any other materials that are present.

In certain embodiments, one or more modified peptides described herein can be provided as a "concentrate", e.g., in a storage container (e.g., in a premeasured volume) ready for dilution, or in a soluble capsule ready for addition to a volume of water, alcohol, hydrogen peroxide, or other diluent.

In certain embodiments, the modified peptides described herein (e.g., one or more esters described above) are preferably suitable for oral administration. In various embodiments, the modified peptide(s) in the oral compositions can be either coated or non-coated. The preparation of enteric-coated particles is disclosed for example in U.S. Pat. Nos. 4,786,505 and 4,853,230.

In various embodiments, compositions contemplated herein typically comprise one or more of the modified peptide(s) described herein (e.g., in any one of Tables 1-5) in an effective amount to achieve a pharmacological effect or therapeutic improvement without undue adverse side effects.

In various embodiments, the typical daily dose of peptide(s) varies and will depend on various factors such as the individual requirements of the patients and the disease to be treated. In various embodiments, the daily dose of compounds can be in the range of 0.1 mg to about 5,000 mg or to about 2,500 mg, or to about 2,000 mg, or to about 1,500 mg, or about 1 mg, or about 5 mg, or about 10 mg, to about 1,000 mg, or about 1 mg, or about 5 mg, or about 10 mg, to about 800 mg, or about 1 mg, or about 5 mg, or about 10 mg to about 600 mg, or about 1 mg, or about 5 mg, or about 10 mg, to about 500 mg, or about 1-500 mg, or 1-400 mg, or 1-300 mg, or 1-200 mg, or 1-100 mg. In one illustrative standard approximate amount of the various modified peptide(s) described above present in the composition can be typically about 0.1 or about 1 to about 100 mg, or to about 400, or to about 1,000, or to about 2,000 mg, more preferably about 5 to 500 mg, and most preferably about 10 to 100 mg administered once a day, in certain embodiments, administered twice a day, in certain embodiments, administered 3 times/day, and in certain embodiments, administered 4, or 6, or 6 or 7, or 8 times/day. In certain embodiments the dosage ranges from about 0.01 or about 0.1, or about 1 mg/kg to about 100 mg/kg, or to about 50 mg/kg, or to about 40 mg/kg, or to about 30 mg/kg, or to about 20 mg/kg, or to about 10 mg/kg, or to about 30 mg/kg, administered once a day, in certain embodiments, administered twice a day, in certain embodiments, administered 3 times/day, and in certain embodiments, administered 4, or 6, or 6 or 7, or 8 times/day.

The active ingredients of the are preferably formulated in a single oral dosage form containing all active ingredients. Such oral formulations include solid and liquid forms. It is noted that solid formulations typically provide improved stability as compared to liquid formulations and can often afford better patient compliance.

In one illustrative embodiment, the one or more of the various modified peptide(s) described above are formulated in a single solid dosage form such as single- or multi-layered tablets, suspension tablets, effervescent tablets, powder, pellets, granules or capsules comprising multiple beads as well as a capsule within a capsule or a double chambered capsule. In another embodiment, the modified peptides may be formulated in a single liquid dosage form such as suspension containing all active ingredients or dry suspension to be reconstituted prior to use.

In certain embodiments, the peptide(s) are formulated as enteric-coated delayed-release granules or as granules coated with non-enteric time-dependent release polymers in order to avoid contact with the gastric juice. Non-limiting examples of suitable pH-dependent enteric-coated polymers are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark EUDRAGIT L 100-55®. This coating can be spray coated onto a substrate.

Illustrative non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the modified peptide is slowly released from the particles by diffusion or following slow erosion of the particles in the stomach.

Illustrative non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the EUDRAGIT® brand polymers. Other film-forming materials can be used alone or in combination with each other or with the ones listed above. These other film forming materials generally include, for example, poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials suitable for making the time-dependent release coating of the compounds described herein include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include, but are not limited to poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer.

While the compositions and methods are described herein with respect to use in humans, they are also suitable for animal, e.g., veterinary use. Thus certain illustrative organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

These embodiments are intended to be illustrative and to provide proof of principle. Using the methods and examples described herein, numerous stabilized peptides, and alternative stabilization protocols will be available to one of skill in the art.

EXAMPLES

The following examples are offered to illustrate, but not to limit the claimed invention.

Example 1

Peptide Stabilization Through thioArylBridging

To meet the initial conditions of low price and commercial availability of all compounds necessary to perform peptide stabilization, it was decided to focus on the use of Cys residues in combination with efficient S-alkylation by dihalogeno-derivatives of aromatic compounds. Use of aromatic compounds was prompted by both low cost and wide range of various analogues available. An additional benefit seemed to also be an increased rigidity of the bridge. Cys residues may be placed in positions analogous to that of olefinoamino acids in stapling approach, with additional flexibility provided by the use of different combinations of (L)Cys, (D)Cys, (L)homoCys, (D)homoCys, (L)Pen, and (D)Pen (all commercially available). S-alkylation was performed using a modified protocol described by *Salvatore and co-workers* (*Tetrahedron Lett* 2005:46,8931) which was adapted to the peptides.

To test the utility of this approach it was decided to modify/stabilize PMI-NBA, the potent dual-specific antagonist of p53-MDM2/MDMX interactions with respective $K_d$ values of 490 pM and 2.4 nM. PMI and its derivative PMI-N8A were originally developed in Lu's group using phage display (*PNAS* 2009:106,4665; *J. Mol. Biol.* 2010: 398,200). Analogous all-D-peptide inhibitors called $^D$PMI-a and $^D$PMI-b were also discovered at the same group using mirror-image phage display (*PNAS* 2010:107,14321) and subsequently tested in an animal model. However even proteolysis resistant $^D$PMI-a required a liposomal delivery system.

TABLE 1

List of tAB-ed derivatives of PMI-N8A

| Peptide | Sequence Residues: neutral, moderately important, significant, critical | SEQ ID NO |
|---|---|---|
| PMI_N8A | Thr-Ser-Phe-Ala-Glu-Tyr-Trp-Ala-Leu-Leu-Ser-Pro | 2 |
| (15-29)p53 | Ser-Gln-Glu-Thr-Phe-Ser-Asp-Leu-Trp-Lys-Leu-Leu-Pro-Glu-Asn | 3 |
| ArB14o | Thr-Ser-Phe-Ala-Cys-Tyr-Trp-Cys-Ala-Leu-Ser-Pro | 4 |

TABLE 1-continued

List of tAB-ed derivatives of PMI-N8A

| Peptide | Sequence Residues: neutral, moderately important, significant, critical | SEQ ID NO |
|---|---|---|
| ArB14Ao | Thr-Ser-PhF-Ala-Cys-Tyr-Nal-Cys-Ala-Cha-Ser-Pipz | 5 |
| ArB14Bo | Arg-Arg-Na2-Arg-Cys-Tyr-Nal-Cys-Arg-Cha-Arg-DISC | 6 |
| ArB14Co | Arg-Arg-PhF-Arg-Cys-Tyr-Nal-Cys-Arg-Cha-Arg-DISC | 7 |
| ArB14Co-AZT | AZT-Arg-Arg-PhF-Arg-Cys-Tyr-Nal-Cys-Arg-Cha-Arg-DISC | 8 |
| ArB14Co-CLB | CLB-Ahx-Arg-Arg-PhF-Arg-Cys-Tyr-Nal-Cys-Arg-Cha-Arg-DISC | 9 |
| ArB14Co-Ch | Chol-Ahx-Lys-Ahx-Arg-Arg-PhF-Arg-Cys-Tyr-Nal-Cys-Arg-Cha-Arg-DISC | 10 |
| ArB14C-Ch/CLB | Chol-Ahx-Lys$^{CLB}$-Ahx-Arg-Arg-PhF-Arg-Cys-Tyr-Nal-Cys-Arg-Cha-Arg-DISC | 11 |
| ArB14Co-MTX | MTX-Ahx-Arg-Arg-PhF-Arg-Cys-Tyr-Nal-Cys-Arg-Cha-Arg-DISC | 12 |
| ArB14Co-TFA | Tfa-Arg-Arg-PhF-Arg-Cys-Tyr-Nal-Cys-Arg-Cha-Arg-DISC | 13 |
| ArB14Dm | Thr-Ser-Phe-Arg-Arg-Tyr-Cys-Arg-Arg-Cys-Ser-Pro | 14 |
| ArB14Em | Thr-Ser-Phe-Arg-Arg-Tyr-Cys-Arg-Arg-Cys-Ser-Pro | 15 |
| ArB14Dmx | Thr-Ser-Phe-Arg-Arg-Tyr-Cys-Arg-Arg-Cys-Ser-Pro | 16 |
| ArB14Emx | Thr-Ser-Phe-Arg-Arg-Tyr-Cys-Arg-Arg-Cys-Ser-Pro | 17 |
| ArB15Am | Thr-Ser-Phe-Ala-Cys-Tyr-Trp-Gly-Cys-Leu-Ser-Pro | 18 |
| ArB15Bm | Thr-Ser-Phe-Ala-Cys-Tyr-Trp-Gly-Cys-Leu-Ser-Pro | 19 |
| ArB15Cp | Thr-Ser-Phe-Ala-Cys-Tyr-Trp-Gly-Cys-Leu-Ser-Pro | 20 |
| ArB15Dp | Thr-Ser-Phe-Ala-Cys-Tyr-Trp-Gly-Cys-Leu-Ser-Pro | 21 |
| ArB15Fo | Arg-Phe-Cys-Arg-Tyr-Trp-Cys-Arg-Leu-Arg-Pro | 22 |
| ArB15Gm | Arg-Phe-Cys-Arg-Tyr-Trp-Cys-Arg-Leu-Arg-Pro | 23 |
| ArB15FNico | Nic-Arg-Phe-Cys-Arg-Tyr-Trp-Cys-Arg-Leu-Arg-Pro | 24 |
| ArB15GNicm | Nic-Arg-Phe-Cys-Arg-Tyr-Trp-Cys-Arg-Leu-Arg-Pro | 25 |
| ArB15F/Gr | Arg-Phe-Cys-Arg-Tyr-Trp-Cys-Arg-Leu-Arg-Pro | 26 |
| ArB15F/GNicr | Nic-Arg-Phe-Cys-Arg-Tyr-Trp-Cys-Arg-Leu-Arg-Pro | 27 |
| ArB15F/Gt | [Arg-Phe-Cys-Arg-Tyr-Trp-Cys-Arg-Leu-Arg-Pro]$_2$Ph(CH$_2$)$_4$ | 28 |
| ArB15F/GNict | [Nic-Arg-Phe-Cys-Arg-Tyr-Trp-Cys-Arg-Leu-Arg-Pro]$_2$Ph(CH$_2$)$_4$ | 29 |

TABLE 1-continued

List of tAB-ed derivatives of PMI-N8A

| Peptide | Sequence Residues: neutral, moderately important, significant, critical | SEQ ID NO |
|---|---|---|
| ArB15F/GO/Nic MiX | [Nic-Arg-Phe-Cys-Arg-Tyr-Trp-Cys-Arg-Leu-Arg-Pro] Ph(CH$_2$)$_4$ [Arg-Phe-Cys-Arg-Tyr-Trp-Cys-Arg-Leu-Arg-Pro] | 30 / 31 |
| ArB15Eb | Thr-Ser-Phe-Ala-Cys-Tyr-Trp-Gly-_Cys_-Leu-Ser-Pro | 32 |
| ArB1 7Ac | Thr-Cys-Phe-Ala-Gly-Tyr-Trp-Cys-_Ala_-Leu-Ser-Pro | 33 |
| ArB17Bc | Thr-Cys-Phe-Ala-Gly-Tyr-Trp-Cys-_Ala_-Leu-Ser-Pro | 34 |
| ArB18Ac | Thr-Cys-Phe-Ala-Gly-Tyr-Trp-Gly-_Cys_-Leu-Ser-Pro | 35 |
| ArB18Bc | Thr-Cys-Phe-Ala-Gly-Tyr-Trp-Gly-_Cys_-Leu-Ser-Pro | 36 |
| ArBMim | [-Bmpa-bhPro-Arg-Ala-_Trp_-Arg-_Lys_-Inp-CH$_2$CH$_2$CH$_2$CH$_2$-S-]$_2$ | 37 |

Abbreviations: Na2-2-Naphthyl-(L)-alanine; Na1-1-Naphthyl-(L)-alanine; PhF-Pentafluoro-(L)-phenylalanine; Cha-Cyclohexyl-(L)-alanine; Nic-Nicotinic acid; DISC-(R,S)-1,3-dihydro-2H-isoindole carboxylic acid; Pipz-Piperazide; Tfa-Tfrifluoroacetic acid; Bmpa-4-(Bromomethyl)phenylacetic acid; bhPro-β-homo-(L)-proline; Inp-isonipecotic acid, CLB-chlorambucil, Ch-cholesterol, MTX-methotrexate.
D-amino acids are underlined cursive e.g. _Cys_. All peptides were synthesized as C-terminal amides except ArB14A (piperazide). Small letter at the end of peptide's name indicates that peptide was tAB-ed using: (o)1,2-Bis(bromomethyl)benzene; (m)1,3-Bis(bromomethyl)benzene; (p)1,4-Bis(bromomethyl)benzene; (b)1-(Bromomethyl)-3[3-(bromomethyl)benzyl]benzene; (c)1-(Chloromethyl)-4[4-(chloromethyl)phenoxy]benzene; (t)peptide was stapled and dimerized using 1,2,4,5-Tetrakis (bromomethyl)benzene.
(r) reduced/not stapled peptide.
(x) thioether groups were oxidized to sulfones.

TABLE 2

Sequences of synthesized ArB peptides.

| Name | Sequence (neutral residues, moderately important, significant residues, critical residues) | Composition | MW Calc/Found | R$_T$ (min) | EC$_{50}$ [μM] HCT-116 |
|---|---|---|---|---|---|
| PMI_M | Thr-Ser-Phe-Ala-Glu-Tyr-Trp-Ala-Leu-Leu-Ser-Pro (SEQ ID NO:2) | C$_{67}$H$_{94}$N$_{14}$O$_{18}$ | 1383.56/1383.59 | 38.17* | 178.8 |
| (15-29)p53 | Ser-Gln-Glu-Thr-Phe-Ser-Asp-Leu-Trp-Lys-Leu-Leu-Pro-Glu-Asn (SEQ ID NO:3) | C$_{82}$H$_{124}$N$_{20}$O$_{26}$ | 1806.00/1806.88 | 37.32* | NA |
| ArB14o | Thr-Ser-Phe-Ala-_Cys_-Tyr-Trp-Cys-_Ala_-Leu-Ser-Pro (SEQ ID NO:4) | C$_{70}$H$_{92}$N$_{14}$O$_{16}$S$_2$ | 1449.71/1449.86 | 39.38* | 248.6 |
| ArB14Ao | Thr-Ser-PhF-Ala-_Cys_-Tyr-Na1-Cys-_Ala_-Cha-Ser-Pipz (SEQ ID NO:5) | C$_{74}$H$_{92}$N$_{13}$O$_{15}$F$_5$S$_2$ | 1562.74/1562.46 | 45.71* | 83.3 |
| ArB14Bo | _Arg_-Arg-Na2-Arg-_Cys_-Tyr-Na1-Cys-_Arg_-Cha-Arg-DISC (SEQ ID NO:6) | C$_{97}$H$_{132}$N$_{28}$O$_{13}$S$_2$ | 1962.41/1962.36 | 37.05 | 10.7 ± 0.7 |
| ArB14Co | _Arg_-Arg-PhF-Arg-_Cys_-Tyr-Na1-Cys-_Arg_-Cha-Arg-DISC (SEQ ID NO:7) | C$_{93}$H$_{125}$N$_{28}$O$_{13}$F$_5$S$_2$ | 2002.30/2003.02 | 36.94 | 11.2 ± 1.2 |
| ArB14Co-AZT | AZT-_Arg_-Arg-PhF-Arg-_Cys_-Tyr-Na1-Cys-_Arg_-Cha-Arg-DISC (SEQ ID NO:8) | C$_{113}$H$_{153}$N$_{30}$O$_{15}$Cl$_2$F$_5$S$_2$ | 2363.66/2364.12 | 37.96 | 30.2 ± 2.5 |
| ArB14Co-CLB | CLB-Ahx-_Arg_-Arg-PhF-Arg-_Cys_-Tyr-Na1-Cys-_Arg_-Cha-Arg-DISC (SEQ ID NO:9) | C$_{113}$H$_{153}$N$_{30}$O$_{15}$Cl$_2$F$_5$S$_2$ | 2401.66/2402.78 | 56.41 | 7.5 ± 1.1 |
| ArB14Co-Ch | Ch-Ahx-Lys-Ahx-_Arg_-Arg-PhF-Arg-_Cys_-Tyr-Na1-Cys-_Arg_-Cha-Arg-DISC (SEQ ID NO:10) | C$_{139}$H$_{203}$N$_{32}$O$_{18}$F$_5$S$_2$ | 2769.45/2769.14 | 57.99 | NT |
| ArB14Co-Ch/CLB | Ch-Ahx-Lys$^{CLB}$-Ahx-_Arg_-Arg-PhF-Arg-_Cys_-Tyr-Na1-Cys-_Arg_-Cha-Arg-DISC (SEQ ID NO:11) | C$_{153}$H$_{220}$N$_{33}$O$_{19}$Cl$_2$F$_5$S$_2$ | 3055.65/3057.04 | 58.30 | NT |

TABLE 2-continued

Sequences of synthesized ArB peptides.

| Name | Sequence (neutral residues, moderately important, significant residues, critical residues) | Composition | MW Calc/Found | $R_T$ (min) | $EC_{50}$ [μM] HCT-116 |
|---|---|---|---|---|---|
| ArB14Co-MTX | MTX-Ahx-*Arg*-Arg-PhF-Arg-*Cys*-Tyr-Nal-Cys-*Arg*-Cha-Arg-DISC (SEQ ID NO:12) | $C_{119}H_{156}N_{37}O_{18}F_5S_2$ | 2551.89/2553.86 | 46.51 | 6.9 ± 0.4 |
| ArB14Co-TFAo | Tfa-*Arg*-Arg-PhF-Arg-*Cys*-Tyr-Nal-Cys-*Arg*-Cha-Arg-DISC (SEQ ID NO:13) | $C_{95}H_{124}N_{28}O_{14}F_8S_2$ | 2098.31/2098.91 | 38.00 | 18.7 ± 3.4 |
| ArB14Dm | Thr-Ser-Phe-Arg-Arg-Tyr-Cys-Arg-Arg-Cys-Ser-Pro (SEQ ID NO:14) | $C_{71}H_{109}N_{25}O_{16}S_2$ | 1632.92/1632.89 | 28.59* | 118.3 |
| ArB14Em | Thr-Ser-Phe-Arg-Arg-Tyr-Cys-Arg-Arg-*Cys*-Ser-Pro (SEQ ID NO:15) | $C_{71}H_{109}N_{25}O_{16}S_2$ | 1632.92/1633.52 | 28.17* | 113.9 |
| ArB14Dmx | Thr-Ser-Phe-Arg-Arg-Tyr-Cys-Arg-Arg-Cys-Ser-Pro (Ox) (SEQ ID NO:16) | $C_{71}H_{109}N_{25}O_{20}S_2$ | 1696.92/1696.72 | 24.00* | 141.5 |
| ArB14Emx | Thr-Ser-Phe-Arg-Arg-Tyr-Cys-Arg-Arg-*Cys*-Ser-Pro (Ox) (SEQ ID NO:17) | $C_{71}H_{109}N_{25}O_{20}S_2$ | 1696.92/1697.21 | 24.79* | NA |
| ArB15Am | Thr-Ser-Phe-Ala-*Cys*-Tyr-Trp-Gly-*Cys*-Leu-Ser-Pro (SEQ ID NO:18) | $C_{69}H_{90}N_{14}O_{16}S_2$ | 1435.68/1436.82 | 40.10 | NA |
| ArB15Bm | Thr-Ser-Phe-Ala-Cys-Tyr-Trp-Gly-*Cys*-Leu-Ser-Pro (SEQ ID NO:19) | $C_{69}H_{90}N_{14}O_{16}S_2$ | 1435.68/1436.59 | 41.01 | NA |
| ArB15Cp | Thr-Ser-Phe-Ala-*Cys*-Tyr-Trp-Gly-*Cys*-Leu-Ser-Pro (SEQ ID NO:20) | $C_{69}H_{90}N_{14}O_{16}S_2$ | 1435.68/1436.04 | 40.07 | >250 |
| ArB15Dp | Thr-Ser-Phe-Ala-Cys-Tyr-Trp-Gly-*Cys*-Leu-Ser-Pro (SEQ ID NO:21) | $C_{69}H_{90}N_{14}O_{16}S_2$ | 1435.68/1436.67 | 39.99 | NA |
| ArB15Fo | Arg-Phe-Cys-Arg-Tyr-Trp-Cys-Arg-Leu-Arg-Pro (SEQ ID NO:22) | $C_{78}H_{113}N_{25}O_{12}S_2$ | 1657.03/1657.86 | 32.64 | 49.64 |
| ArB15Gm | Arg-Phe-Cys-Arg-Tyr-Trp-Cys-Arg-Leu-Arg-Pro (SEQ ID NO:23) | $C_{78}H_{113}N_{25}O_{12}S_2$ | 1657.03/1657.46 | 31.92 | 52.19 |
| ArB15FNicoNic | Arg-Phe-Cys-Arg-Tyr-Trp-Cys-Arg-Leu-Arg-Pro (SEQ ID NO:24) | $C_{84}H_{116}N_{26}O_{13}S_2$ | 1762.13/1763.63 | 35.97 | 189.0 |
| ArB15GNicmNic | Arg-Phe-Cys-Arg-Tyr-Trp-Cys-Arg-Leu-Arg-Pro (SEQ ID NO:25) | $C_{84}H_{116}N_{26}O_{13}S_2$ | 1762.13/1762.51 | 35.36 | 126.4 |
| ArB15F/Gr | Arg-Phe-Cys-Arg-Tyr-Trp-Cys-Arg-Leu-Arg-Pro (SEQ ID NO:26) | $C_{70}H_{107}N_{25}O_{12}S_2$ | 1554.89/1555.39 | 25.06* | >250 |
| ArB15F/GNicr | Nic-Arg-Phe-Cys-Arg-Tyr-Trp-Cys-Arg-Leu-Arg-Pro (SEQ ID NO:27) | $C_{76}H_{110}N_{26}O_{13}S_2$ | 1659.99/1660.56 | 28.24* | 64.5 |
| ArB15F/Gt | [Arg-Phe-Cys-Arg-Tyr-Trp-Cys-Arg-Leu-Arg-Pro]$_2$Ph(CH$_2$)$_4$ (SEQ ID NO:28) | $C_{150}H_{220}N_{50}O_{24}S_4$ | 3235.95/3235.80 | 30.72 | NT |

TABLE 2-continued

Sequences of synthesized ArB peptides.

| Name | Sequence (neutral residues, moderately important, significant residues, critical residues) | Composition | MW Calc/ Found | $R_T$ (min) | $EC_{50}$ [µM] HCT-116 |
|---|---|---|---|---|---|
| ArB15F/GNict | [Nic-Arg-Phe-Cys-Arg-Tyr-Trp-Cys-Arg-Leu-Arg-Pro]$_2$Ph(CH$_2$)$_4$ (SEQ ID NO:29) | $C_{162}H_{226}N_{52}O_{26}S_4$ | 3446.14/ 3447.36 | 33.62 | NT |
| ArB15F/ G0/Nic Mix | [Nic-Arg-Phe-Cys-Arg-Tyr-Trp-Cys-Arg-Leu-Arg-Pro]Ph(CH$_2$)$_4$ (SEQ ID NO:30) [Arg-Phe-Cys-Arg-Tyr-Trp-Cys-Arg-Leu-Arg-Pro] (SEQ ID NO:31) | $C_{156}H_{223}N_{51}O_{25}S$ | 3341.05/ 3341.51 | 34.42* 34.86* | NT |
| ArB15Eb | Thr-Ser-Phe-Ala-Cys-Tyr-Trp-Gly-Cys-Leu-Ser-Pro (SEQ ID NO:32) | $C_{76}H_{96}N_{14}O_{16}S_2$ | 1525.81/ 1526.03 | 46.95 | 162.9 |
| ArB17Ac | Thr-Cys-Phe-Ala-Gly-Tyr-Trp-Cys-*Ala*-Leu-Ser-Pro (SEQ ID NO:33) | $C_{75}H_{94}N_{14}O_{16}S_2$ | 1511.78/ 1511.01 | 44.24 | NA |
| ArB17Bc | Thr-Cys-Phe-Ala-Gly-Tyr-Trp-Cys-*Ala*-Leu-Ser-Pro (SEQ ID NO:34) | $C_{75}H_{94}N_{14}O_{16}S_2$ | 1511.78/ 1511.26 | 45.53 | NA |
| ArB18Ac | Thr-Cys-Phe-Ala-Gly-Tyr-Trp-Gly-*Cys*-Leu-Ser-Pro (SEQ ID NO:35) | $C_{74}H_{92}N_{14}O_{16}S_2$ | 1497.75/ 1499.28 | 42.66 | NA |
| ArB18Bc | Thr-Cys-Phe-Ala-Gly-Tyr-Trp-Gly-*Cys*-Leu-Ser-Pro (SEQ ID NO:36) | $C_{74}H_{92}N_{14}O_{16}S_2$ | 1497.75/ 1498.49 | 45.85 | NA |
| ArBMim | [-Bmpa-bhPro-Arg-Ala-*Trp*-Arg-*Lys*-Inp-CH$_2$CH$_2$CH$_2$CH$_2$-S-]$_2$ (SEQ ID NO:37) | $C_{114}H_{172}N_{32}O_{16}S_2$ | 2310.94/ 2311.61 | 33.70* | 23.4 ± 2.1 |

Abbreviations: Na2-2-Naphthyl-(L)-alanine; Na1-1-Naphthyl-(L)-alanine; PhF-Pentafluoro-(L)-phenyl-alanine; Cha-Cyclohexyl-(L)-alanine; Nic-Nicotinic acid; DISC-(R,S)-1,3-dihydro-2H-isoindole carbox-ylic acid; Pipz-Piperazide; Tfa-Tfrifluoroacetic acid; Bmpa-4-(Bromomethyl)phenylacetic acid; bhPro-β-homo-(L)-proline; Inp-isonipecotic acid.
D-amino acids are underlined cursive e.g. *Cys*. All peptides were synthesized as C-terminal amides except ArB14A- that was synthesized as C-terminal piperazide (Pipz).
Small letter at the end of peptide's name indicates that peptide was tAB-ed using: o-1,2-Bis (bromomethyl)benzene; m-1,3-Bis(bromomethyl)benzene; p-1,4-Bis(bromomethyl)benzene; b-1-(Bromom-ethyl)-3-[3-(bromomethyl)benzyl]benzene; c-1-(Chloromethyl)-4-[4-(chloromethyl)phenoxy]benzene; t-peptide was stapled and dimerized using 1,2,4,5- Tetrakis(bromomethyl)benzene.
r-reduced/not stapled peptide.
x-thioether groups were oxidized to sulfones.
*-Vydac C18 analytical column (other: Waters Symmetry C18 column).
NA-not active; NT-not tested.

Based on analysis of p53/MDM2 and PMI-N8A/MDM2 crystal structures we placed various combinations of (L)- and (D)Cys residues in specific positions of PMI sequence considering the importance of particular amino acids for peptide bioactivity (see, e.g., Tables 1 and 2. Particular combinations were in turn tAB-ed using selected bis-halogeno-aryl compounds (see, e.g., FIG. 1) that fit into spatial arrangements/dimensions available, based on computer aided molecular modeling. Since $^D$PMI-a presumably lack cell permeating properties, in addition we engineered several analogues as a cell permeating compounds containing multiple Arg residues simultaneously employing combination of D- and unusual amino acids to further enhance stability and binding properties of the peptide. Analogues were subsequently tested in vitro using HCT116 colorectal cancer cells and PrestoBlue™ assay (Invitrogen). The most active compound (ArB14Co) was subsequently chosen for second round of modifications resulting in conjugates with AZT ("click" reaction), chlorambucil (CLB), methotrexate (MTX), and cholesterol (Chol, see Table 1). Selected analogues were also tested in vivo using mouse subcutaneous engraftment model (HCT116/SCID).

Multimerization of peptides is frequently used as a means to increase immunogenicity (MAP peptides), prolong serum half-life/stability or way to increase affinity to the receptor by harnessing multivalency effects. One of such examples was recently described (*J. Med. Chem.* 2011:54,3306) resulting in potent dimeric Smac analogues. During our work we realized that tAB-protocol may be also used for multimerization using halogenomethyl-substituted-aryl ((XCH$_2$)$_n$Ar) compounds that are commercially available.

To test our theory we decided to focus on Smac multimers. First, we synthesized a small library of Smac compounds (see, Tables 3 and 4) varying in position 4 substituents having general structure N-MeAla-Tle-4-(trans-Bn)-Pro-Xaa-NHCH$_2$CH$_2$—SH (SEQ ID NO:38), which were tested in vitro using MDA-MB-231 and MCF-7 breast cancer cell lines and PrestoBlue™ assay (Invitrogen). Secondly, the most active analogues were chosen for oligomerization and further in vitro and in vivo testing.

TABLE 3

Library of Smac compounds, (having structure N-MeAla-Tle-4-(trans-Bn)-Pro-Xaa-NHCH$_2$CH$_2$—SH, (SEQ ID NO:38)). See also FIG. 4.

| Peptide | Xaa | EC$_{50}$ [μM] MDA-MB-231 | EC$_{50}$ [μM] MCF-7 | SEQ ID NO |
|---|---|---|---|---|
| SMAC1 | Phg | 17.2 ± 6.4 | 31.2 ± 1.4 | 39 |
| SMAC2 | NMePhg | 23.8 ± 4.5 | 43.6 ± 1.6 | 40 |
| SMAC3 | Amp | 14.3 ± 3.2 | 49.1 ± 2.6 | 41 |
| SMAC4 | DISC | 47.1 ± 15.9 | 41.6 ± 3.7 | 42 |
| SMAC5 | Idc | 68.3 ± 4.0 | 476.7 ± 48.4 | 43 |
| SMAC6 | Chg | 9.8 ± 3.1 | 31.2 ± 2.1 | 44 |
| SMAC7 | Amc | 91.8 ± 16.3 | 86.3 ± 10.5 | 45 |
| SMAC8 | Phe | 34.3 ± 6.7 | 33.3 ± 1.5 | 46 |
| SMAC9 | PhF | 27.0 ± 3.2 | 19.8 ± 3.0 | 47 |
| SMAC10 | bhPhe | 29.7 ± 3.3 | 23.9 ± 2.1 | 48 |
| SMAC11 | Tic | 13.3 ± 1.3 | 5.3 ± 0.6 | 49 |
| SMAC12 | Cha | 10.1 ± 2.6 | 21.2 ± 2.4 | 50 |
| SMAC13 | bh$^1$NalGly | 21.7 ± 1.3 | 12.3 ± 0.5 | 51 |
| SMAC14 | $^1$Nal | 4.5 ± 1.1 | 13.4 ± 0.5 | 52 |
| SMAC14-2X | $^1$Nal | 2.8 ± 0.1 | 3.5 ± 1.6 | 53 |
| SMAC14-3X | $^1$Nal | 7.2 ± 1.5 | 120.4 ± 8.4 | 54 |
| SMAC15 | $^2$Nal | 9.4 ± 0.5 | 10.5 ± 0.6 | 55 |
| SMAC16 | Dpa | 9.4 ± 0.6 | 11.3 ± 1.8 | 56 |
| SMAC17 | Bip | 10.6 ± 0.9 | 5.7 ± 0.9 | 57 |
| *SMAC17-2X | Bip | 2.4 ± 0.3 | 1.7 ± 0.4 | 58 |
| SMAC17-3X | Bip | NA | NA | 59 |
| SMAC18 | Ant | 17.3 ± 1.0 | 15.1 ± 0.9 | 60 |
| SMAC19 | Trp | 36.7 ± 3.2 | 27.6 ± 1.8 | 61 |

TABLE 4

Sequences of synthesized Smac derivatives and additional data.

| Peptide | Sequence | Composition | MW Calc/Found | RT [min] | SEQ ID NO |
|---|---|---|---|---|---|
| SMAC1 | N$^{Me}$Ala-Tle-(4-Bzl)Pro-Phg-NHCH$_2$CH$_2$SH | C$_{32}$H$_{45}$N$_5$O$_4$S | 595.80/595.31 | 39.80* | 39 |
| SMAC2 | N$^{Me}$Ala-Tle-(4-Bzl)Pro-N$^{Me}$Phg-NHCH$_2$CH$_2$SH | C$_{33}$H$_{47}$N$_5$O$_4$S | 609.82/610.11 | 41.03* | 40 |
| SMAC3 | N$^{Me}$Ala-Tle-(4-Bzl)Pro-Amp-NHCH$_2$CH$_2$SH | C$_{33}$H$_{47}$N$_5$O$_4$S | 609.82/609.85 | 35.68* | 41 |
| SMAC4 | N$^{Me}$Ala-Tle-(4-Bzl)Pro-Disc-NHCH$_2$CH$_2$SH | C$_{33}$H$_{45}$N$_5$O$_4$S | 607.81/608.56 | 39.07* | 42 |
| SMAC5 | N$^{Me}$Ala-Tle-(4-Bzl)Pro-Idc-NHCH$_2$CH$_2$SH | C$_{33}$H$_{45}$N$_5$O$_4$S | 607.81/609.62 | 32.08* | 43 |
| SMAC6 | N$^{Me}$Ala-Tle-(4-Bzl)Pro-Chg-NHCH$_2$CH$_2$SH | C$_{32}$H$_{51}$N$_5$O$_4$S | 601.84/601.76 | 41.26* | 44 |
| SMAC7 | N$^{Me}$Ala-Tle-(4-Bzl)Pro-Amc-NHCH$_2$CH$_2$SH | C$_{32}$H$_{51}$N$_5$O$_4$S | 601.84/602.78 | 34.89* | 45 |
| SMAC8 | N$^{Me}$Ala-Tle-(4-Bzl)Pro-Phe-NHCH$_2$CH$_2$SH | C$_{33}$H$_{47}$N$_5$O$_4$S | 609.82/610.78 | 40.82* | 46 |
| SMAC9 | N$^{Me}$Ala-Tle-(4-Bzl)Pro-PhF-NHCH$_2$CH$_2$SH | C$_{33}$H$_{42}$N$_5$O$_4$SF$_5$ | 699.77/701.39 | 48.21* | 47 |
| SMAC10 | N$^{Me}$Ala-Tle-(4-Bzl)Pro-bhPhe-NHCH$_2$CH$_2$SH | C$_{34}$H$_{49}$N$_5$O$_4$S | 623.85/623.44 | 40.29* | 48 |
| SMAC11 | N$^{Me}$Ala-Tle-(4-Bzl)Pro-Tic-NHCH$_2$CH$_2$SH | C$_{34}$H$_{47}$N$_5$O$_4$S | 621.83/623.62 | 41.07* | 49 |
| SMAC12 | N$^{Me}$Ala-Tle-(4-Bzl)Pro-Cha-NHCH$_2$CH$_2$SH | C$_{33}$H$_{53}$N$_5$O$_4$S | 615.87/615.89 | 44.35* | 50 |
| SMAC13 | N$^{Me}$Ala-Tle-(4-Bzl)Pro-bh$^1$NalGly-NHCH$_2$CH$_2$SH | C$_{37}$H$_{49}$N$_5$O$_4$S | 659.88/659.36 | 43.15* | 51 |
| SMAC14 | N$^{Me}$Ala-Tle-(4-Bzl)Pro-$^1$Nal-NHCH$_2$CH$_2$SH | C$_{37}$H$_{49}$N$_5$O$_4$S | 659.88/659.49 | 45.81* | 52 |
| SMAC14-2X | (N$^{Me}$Ala-Tle-(4-Bzl)Pro-$^1$Nal-NHCH$_2$CH$_2$S)$_2$—(CH$_2$)$_2$Ph | C$_{82}$H$_{104}$N$_{10}$O$_8$S$_2$ | 1421.90/1421.13 | 49.99* | 53 |
| SMAC14-3X | (N$^{Me}$Ala-Tle-(4-Bzl)Pro-$^1$Nal-NHCH$_2$CH$_2$S)$_3$—(CH$_2$)$_3$Ph | C$_{120}$H$_{153}$N$_{15}$O$_{12}$S$_3$ | 2093.80/2094.52 | 51.29* | 54 |
| SMAC15 | N$^{Me}$Ala-Tle-(4-Bzl)Pro-$^2$Nal-NHCH$_2$CH$_2$SH | C$_{37}$H$_{49}$N$_5$O$_4$S | 659.88/659.70 | 45.59* | 55 |
| SMAC16 | N$^{Me}$Ala-Tle-(4-Bzl)Pro-Dpa-NHCH$_2$CH$_2$SH | C$_{39}$H$_{51}$N$_5$O$_4$S | 685.92/685.37 | 46.88* | 56 |
| SMAC17 | N$^{Me}$Ala-Tle-(4-Bzl)Pro-Bip-NHCH$_2$CH$_2$SH | C$_{39}$H$_{51}$N$_5$O$_4$S | 685.92/685.43 | 48.11* | 57 |
| SMAC17-2X | (N$^{Me}$Ala-Tle-(4-Bzl)Pro-Bip-NHCH$_2$CH$_2$S)$_2$—(CH$_2$)$_2$Ph | C$_{86}$H$_{108}$N$_{10}$O$_{12}$S$_3$ | 1473.98/1475.54 | 51.45* | 58 |
| SMAC17-3X | (N$^{Me}$Ala-Tle-(4-Bzl)Pro-Bip-NHCH$_2$CH$_2$S)$_3$—(CH$_2$)$_3$Ph | C$_{126}$H$_{159}$N$_{15}$O$_{12}$S$_3$ | 2171.92/2173.25 | 52.89* | 59 |
| SMAC18 | N$^{Me}$Ala-Tle-(4-Bzl)Pro-Ant-NHCH$_2$CH$_2$SH | C$_{41}$H$_{51}$N$_5$O$_4$S | 709.94/709.44 | 50.74* | 60 |

TABLE 4-continued

Sequences of synthesized Smac derivatives and additional data.

| Peptide | Sequence | Composition | MW Calc/ Found | RT [min] | SEQ ID NO |
|---|---|---|---|---|---|
| SMAC19 | N$^{Me}$Ala-Tle-(4-Bzl)Pro-Trp-NHCH$_2$CH$_2$SH | C$_{35}$H$_{48}$N$_5$O$_4$S | 648.86/ 649.05 | 40.68* | 61 |

Abbreviations:
Na2—2-Naphthyl-(L)-alanine;
Na1—1-Naphthyl-(L)-alanine;
PhF—Pentafluoro-(L)-phenylalanine;
Cha—Cyclohexyl-(L)-alanine;
DISC—(R,S)-1, 3-Dihydro-2H-isoindole carboxylic acid;
bhPhe—β-homo-(L)-Phenylalanine;
N$^{Me}$Ala—N-Methyl-(L)-alanine;
N$^{Me}$Phg—N-Methyl-(L)-phenylglycine;
Cha—Cyclohexyl-(L)-glycine;
Tle—(L)-tertLeucine;
(4-Bzl)Pro—trans-4-Benzyl-(L)-proline;
Amp—4-(Aminomethyl)phenylpropionic acid;
Amc—trans-4-(Aminomethyl)cyclohexanoic acid;
Idc—(S)-Indoline-2-carboxylic acid;
Tic—(3S)-1,2,3,4-Tetrahydroisoquinoline-3-carboxylic acid;
bh$^l$ NalGly—β-homo-(S,R)-Naphthylglycine;
Dpa—3,3-Diphenyl-(L)-alanine;
All peptides were synthesized as C-terminal cysteamides.
NA-not active.

Cell viability assay experiments for Smac analogues is shown in FIG. 12.

The tAB approach is also applicable to β-hairpin peptides. We used our potent anti-influenza/anti-HIV β-hairpin analogue DpV13 (J. Immunol. 2012:188,2759) as a scaffold for tAB modification. The obtained compound was subsequently oxidized using OXONE® in 75% MeOH/water mix/3h. The compounds were subsequently tested in vitro against HIV-1 using TZMB1 assay (see, FIG. 6).

More then one tAB can be introduced into one sequence in solution with no need for side chains protection. We used analogue of L4F (apoAI-mimetic peptide) to test feasibility of this idea (see, FIGS. 7A and 7B).

TABLE 5

Sequences of synthesized derivatives of L4F

| Name | Sequence | Composition | MW Calc/ Found | R$_T$ (min) | SEQ ID NO |
|---|---|---|---|---|---|
| ArB-4Fr | Ac-D-Na1-FK-_Cys_-FY-Cys-KVAE-_Cys_-FK-Cys-AF-CONH$_2$ | C$_{110}$H$_{148}$N$_{22}$O$_{24}$S$_4$ | 2290.77/ 2291.87 | 46.23 | 62 |
| ArB-4Fo | Ac-D-Na1-FK-_Cys_-FY-Cys-KVAE-_Cys_-FK-Cys-AF-CONH$_2$ | C$_{126}$H$_{160}$N$_{22}$O$_{24}$S$_{42}$ | 2495.04/ 2496.19 | 50.07 | 63 |
| ArB-4Fox | Ac-D-Na1-FK-_Cys_-FY-Cys-KVAE-_Cys_-FK-Cys-AF-CONH$_2$ | C$_{126}$H$_{160}$N$_{22}$O$_{32}$S$_4$ | 2623.03/ 2624.24 | 44.70 | 64 |
| DpV13 | Ile-Cys-Arg-Ile-Ile-Ile-_Pro_-Pro-Ile-Arg-Ile-Ile-Cys-CONH$_2$ | C$_{70}$H$_{126}$N$_{20}$O$_{13}$S$_2$ | 1520.01/ 1520.20 | 43.23 | 65 |
| DpV13ST | Ile-Cys-Arg-Ile-Ile-Ile-_Pro_-Pro-Ile-Arg-Ile-Ile-Cys-CONH$_2$ | C$_{78}$H$_{134}$N$_{20}$O$_{13}$S$_2$ | 1624.16/ 1625.37 | 47.48 | 66 |
| DpV13STOX | Ile-Cys-Arg-Ile-Ile-Ile-_Pro_-Pro-Ile-Arg-Ile-Ile-Cys-CONH$_2$ | C$_{78}$H$_{134}$N$_{20}$O$_{17}$S$_2$ | 1688.16/ 1689.58 | 43.81 | 67 |
| PalHemArB | Pal-Ahx-TYSLHCGPRTCVVRPK | C$_{112}$H$_{179}$N$_{27}$O$_{22}$S$_2$ | 2319.94/ 2321.08 | 50.58 | 68 |
| PalHemArB2 | [Pal-Ahx-TYSLHCGPRTCVVRPK]$_2$Sub | C$_{232}$H$_{368}$N$_{54}$O$_{46}$S$_4$ | 4778.04/ 4777.56 | 58.83 | 69 |

Abbreviations: Na1-1-Naphthyl-(L)-alanine; Sub-Suberic acid; Pal-Palmitic acid; Ahx-6-amino-hexanoic acid;
D-amino acids are underlined cursive e.g. _Cys_.

Theoretically, in certain cases, the use of tAB approach may be combined with structural features of parental molecules to minimize its unwanted "interference". After analysis of crystal structures of EPO/EPOR interactions and EPO-mimetic peptides, we synthesized, tAB-ed and dimerized (suberate) a Hematide™ analogue with the replacement of 2 aromatic core residues by one tAB-linker afforded by 1,2-bis(bromomethyl)naphthalene (see FIG. 8).

Conclusions

The bis(thioether)-Aryl-Bridge (tAB™) approach can be successfully used to stabilize α-helical peptides, β-hairpin peptides and for multimerization.

Reaction can be carried out on solid support as well as in solution (including water based compositions) using fully deprotected analogues.

Obtained novel analogues possess biological activity proving that tAB™ technology is applicable in biological systems.

Example 2

Determination of In Vitro Antiviral Activity of Test Materials Evaluated Against SARS-CoV Strains Introduction The following test is essentially as described by Sidwell and Huffman (Sidwell and Huffman (1971) *Appl. Microbiol.* 22: 797-801), and was used in the reports on the in vitro antiviral activity of several compounds (Barnard et al. (2006) *Antivir. Chem. Chemother.*, 17: 275-284; Barnard et al. (2004) *Antivir. Chem. Chemother.*, 15: 15-22). All procedures involving virus were done in a BSL-3 laboratory with restricted access. All personnel wore protective body suits and were equipped with positive air pressure respirators.

Materials and Methods:

Cells and Virus

African green monkey kidney cells (Vero E6 cells) were obtained from Centers for Disease Control (CDC, Atlanta, Ga.) from American Type Culture Collection (ATCC, Manassas, Va.). The cells were grown in minimal essential medium (MEM, Gibco-BRL, Gaithersburg, Md.) supplemented with 0.1% $NaHCO_3$ and 10% fetal bovine serum (FBS, Hyclone Laboratories, Logan, Utah). When performing antiviral assays, serum was reduced to 2%, and 50 µg/ml gentamicin (Sigma Chemical Company, St. Louis, Mo.) was added to the medium.

SARS coronavirus (SARS-CoV), strain Urbani, was obtained from Centers for Disease Control (Atlanta, Ga.).

Preparation of Compounds for Testing

Compounds in solution were diluted in test medium (MEM without serum) through a series of four or eight ½ $log_{10}$ dilutions for evaluation. A SARS-CoV protease inhibitor (Sui Xiong Cai, Maxim Pharmaceuticals, San Diego, Calif.) was used as a positive control for virus inhibition.

Antiviral Testing Procedure

Cytopathic Effect (CPE) Inhibition (Visual) Assay

Cells were seeded to 96-well flat-bottomed tissue culture plates (Corning Glass Works, Corning, N.Y.), 0.2 ml/well, at the proper cell concentration, and incubated overnight at 37° C. in order to establish a cell monolayer. When the monolayer was established, the growth medium was decanted and the various dilutions of test compound were added to each well (3 wells/dilution, 0.1 ml/well). Compound diluent medium was added to cell and virus control wells (0.1 ml/well). Virus (viral MOI=0.001), diluted in test medium, was added to compound test wells (3 wells/dilution of compound) and to virus control wells at 0.1 ml/well. Virus was added approximately 5 min after compound. Test medium without virus was added to all toxicity control wells (2 wells/dilution of each test compound) and to cell control wells at 0.1 ml/well. The plates were incubated at 37° C. in a humidified incubator with 5% $CO_2$, 95% air atmosphere until virus control wells had adequate cytopathic effect (CPE) readings. This was achieved in 3 days after virus exposure to cells. Cells were then examined microscopically for CPE, this being scored from 0 (normal cells) to 4 (maximal, 100%, CPE). The cells in the toxicity control wells were observed microscopically for morphologic changes attributed to cytotoxicity. This cytotoxicity was also graded at T (100% toxicity, complete cell sloughing from plate), $P_{VH}$ (80% cytotoxicity), $P_H$ (60% cytotoxicity), P (40% cytotoxicity), $P_{SI}$ (20% cytotoxicity), and 0 (normal cells). The 50% effective dose (EC50) and 50% cytotoxic dose (IC50) was calculated by regression analysis of the virus CPE data and the toxicity control data, respectively. The therapeutic index (SI) for each compound tested was calculated using the formula: SI=IC50÷EC50 (see Table 6).

TABLE 6

Antiviral summary report for SARS-CoV (strain Urbani) in African green monkey kidney cells (Vero 76).

| DpV13 ST (µM) | | | DpV16 (µM) | | |
|---|---|---|---|---|---|
| CC50: | 18, Vis | 44, NR | CC50: | >100, Vis | >100, NR |
| EC50: | 1.8, Vis | 5.6, NR | EC50: | 13, Vis | 12, NR |
| SI: | 10, Vis | 7.9, NR | SI: | >7.7, Vis | >8.3, NR |

SI (Selectivity Index) = CC50 (Toxicity)/EC50 (Antiviral activity)

Neutral Red (NR) Uptake Assay of CPE Inhibition and Compound Cytotoxicity

This assay was done on the same CPE inhibition test plates described above to verify the inhibitory activity and the cytotoxicity observed by visual observation. The usual correlation between visual and neutral red assays in our hands has been greater than 95% (Barnard et al. (2001) *Antivir. Chem. Chemother.*, 12: 241-250). The NR assay was performed using a modified method of Cavenaugh et al. (1990) *New Drugs*, 8: 347-354 as described by Barnard et al. (1997) *Antiviral. Chem. Chemother.*, 8: 223-233. Medium was removed from each well of a plate, 0.034% NRF (0.34% neutral red in PBS supplemented with formalin at 10%) added to each well of the plate and the plate incubated for 2 hr at 37° C. in the dark. The NR solution was then removed from the wells, rinsed and the remaining dye extracted using ethanol buffered with Sörenson's citrate buffer. Absorbances at 540 nm/405 nm were read with a microplate reader (Opsys MR™, Dynex Technologies, Chantilly, Va., USA). Absorbance values are expressed as percents of untreated controls and $EC_{50}$, $IC_{50}$ and SI values were calculated as described above.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A peptide stabilized with at least one bis(thioether)aryl bridge between two S-bearing residues within said peptide, wherein the amino acid sequence of said peptide comprises the sequence of a peptide selected from the group consisting of ArB14Bo (SEQ ID NO:6), ArB14Co (SEQ ID NO:7), ArB14Co-AZT (SEQ ID NO:8), ArB14Co-CLB (SEQ ID NO:9), ArB14Co-Ch (SEQ ID NO:10), ArB14C-Ch/CLB (SEQ ID NO:11), ArB14Co-MTX (SEQ ID NO:12), and ArB14Co-TFA (SEQ ID NO:13).

2. The peptide of claim 1, wherein said S bearing residues are selected from the group consisting of (L)Cys, (D)Cys, (L)homoCys, (D)homoCys, (L)Pen, and (D)Pen.

3. The peptide of claim 1, wherein said peptide is mutated/modified to introduce at least one of said S-bearing residues.

4. The peptide of claim 1, wherein said one bis(thioether) aryl bridge is introduced into said peptide by reacting a peptide lacking said bridge with a di-halogeno-aryl-compounds to form a bis(thioether)-Aryl-Bridge between said two residues.

5. The peptide of claim 4, wherein said di-halogeno-aryl-compound has the formula $XCH_2$—Ar—$CH_2X$, where X is Cl, Br, or I.

6. The peptide of claim 5, wherein X is Cl.

7. The peptide of claim 5, wherein X is Br.

8. The peptide of claim 5, wherein X is I.

9. The peptide of claim 5, wherein said di-halogeno-aryl-compound has a formula selected from the group consisting of

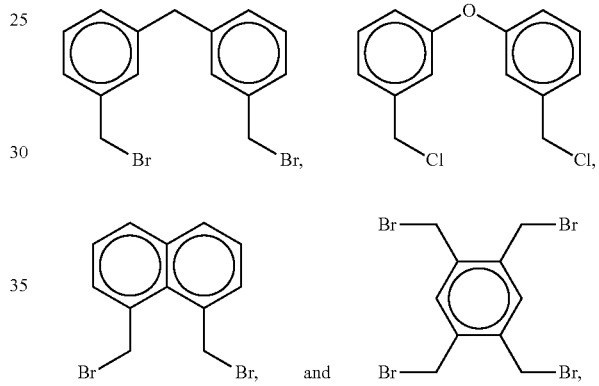

where any of the halogens can be Br, Cl, or I.

10. The peptide of claim 5, wherein said di-halogeno-aryl-compound has a formula selected from the group consisting of

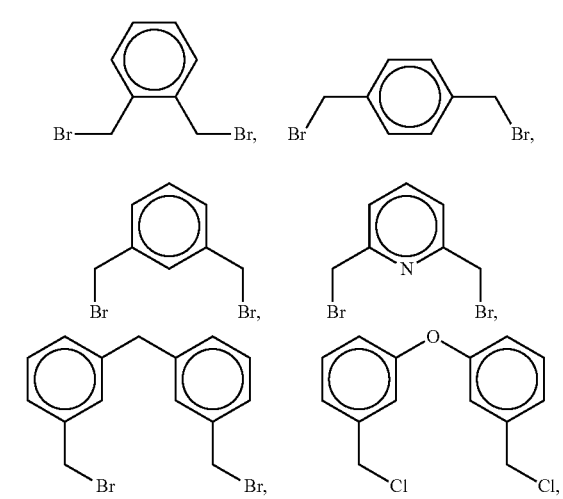

-continued

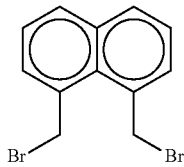 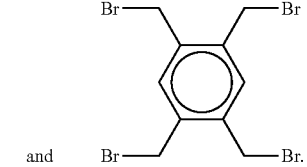

and

11. The peptide of claim 1, wherein said peptide shows improved stability in solution as compared to the same peptide lacking said bridge(s).

12. The peptide of claim 1, wherein said peptide shows increased serum half-life in vivo as compared to the same peptide lacking said bridge(s).

13. The peptide of claim 1, wherein said peptide shows increased bioavailability in vivo as compared to the same peptide lacking said bridge(s).

14. The peptide of claim 1, wherein said peptide is ArB14Bo.

15. The peptide of claim 1, wherein said peptide is AR14Co.

* * * * *